US011285170B2

(12) United States Patent
Tets et al.

(10) Patent No.: US 11,285,170 B2
(45) Date of Patent: Mar. 29, 2022

(54) FRACTIONATED ANTIMICROBIAL COMPOSITIONS AND USE THEREOF

(71) Applicants: Viktor Veniaminovich Tets, New York, NY (US); Georgy Viktorovich Tets, New York, NY (US)

(72) Inventors: Viktor Veniaminovich Tets, New York, NY (US); Georgy Viktorovich Tets, New York, NY (US); Konstantin Andreevich Krasnov, St. Petersburg (RU)

(73) Assignees: Viktor Veniaminovich TETS, St. Petersburg (RU); Georgy Viktorovich TETS, St. Petersburg (RU)

( * ) Notice: Subject to any disclaimer, the term of this patent is extended or adjusted under 35 U.S.C. 154(b) by 88 days.

(21) Appl. No.: 16/616,325

(22) PCT Filed: May 22, 2018

(86) PCT No.: PCT/US2018/033880
§ 371 (c)(1),
(2) Date: Nov. 22, 2019

(87) PCT Pub. No.: WO2018/217743
PCT Pub. Date: Nov. 29, 2018

(65) Prior Publication Data
US 2020/0113932 A1 Apr. 16, 2020

Related U.S. Application Data

(60) Provisional application No. 62/633,761, filed on Feb. 22, 2018, provisional application No. 62/510,446, filed on May 24, 2017.

(51) Int. Cl.
| | | |
|---|---|---|
| *A61K 31/785* | (2006.01) |
| *A61P 31/12* | (2006.01) |
| *A61P 31/04* | (2006.01) |
| *A61P 31/10* | (2006.01) |
| *A61P 35/00* | (2006.01) |
| *A61K 45/06* | (2006.01) |
| *C08G 73/08* | (2006.01) |

(52) U.S. Cl.
CPC ............ *A61K 31/785* (2013.01); *A61K 45/06* (2013.01); *A61P 31/04* (2018.01); *A61P 31/10* (2018.01); *A61P 31/12* (2018.01); *A61P 35/00* (2018.01); *C08G 73/08* (2013.01)

(58) Field of Classification Search
CPC combination set(s) only.
See application file for complete search history.

(56) References Cited

U.S. PATENT DOCUMENTS

| 8,993,712 B2 | 3/2015 | Loy et al. |
| 2002/0010150 A1 | 1/2002 | Cortese et al. |
| 2004/0082925 A1 | 4/2004 | Patel |
| 2006/0079503 A1 | 4/2006 | Schwede et al. |
| 2011/0269936 A1 | 11/2011 | Tets et al. |
| 2013/0096062 A1 | 4/2013 | Hedrich et al. |
| 2013/0150451 A1 | 6/2013 | Salamone et al. |
| 2014/0023714 A1 | 1/2014 | Gagnieu et al. |
| 2015/0038512 A1* | 2/2015 | Looper .................. A01N 47/12 514/239.5 |

FOREIGN PATENT DOCUMENTS

| CN | 102453315 A | 5/2012 |
| CN | 103705535 A | 4/2014 |
| RU | 2039735 C1 | 7/1995 |
| RU | 2141452 C1 | 11/1999 |
| RU | 2176523 C2 | 12/2001 |
| RU | 2176651 C2 | 12/2001 |
| RU | 2230734 C1 | 6/2004 |
| RU | 2004135533 A | 7/2005 |
| RU | 2006122738 | 1/2008 |
| RU | 2324478 C2 | 5/2008 |
| RU | 2422137 C1 | 6/2011 |
| RU | 2423359 C1 | 7/2011 |
| RU | 2480227 C2 | 4/2013 |
| RU | 2533232 C2 | 1/2014 |
| RU | 2012130924 A | 1/2014 |
| RU | 2546006 C1 | 4/2015 |
| WO | 1996028570 A1 | 9/1996 |
| WO | 199918232 A1 | 4/1999 |
| WO | 2001082937 A1 | 11/2001 |
| WO | 20030093249 A1 | 11/2003 |
| WO | 2008008912 A1 | 1/2008 |
| WO | 2011135577 A1 | 11/2011 |
| WO | 2013053753 A2 | 4/2013 |
| WO | 2016118043 A1 | 7/2016 |

OTHER PUBLICATIONS

RU2422137C1 Machine Translation (Year: 2011).*
Bailey, Andrew and Longson, Maurice, "Virucidal activity of chlorhexidine on strains of Herpesvirus hominis, poliovirus, and adenovirus", Journal of Clinical Pathology (1972), vol. 25 pp. 76-78.
Communication (Extended European Search Report) issued by the European Patent Office in European Patent Application No. 15879124.1, dated Sep. 20, 2018, 6 pages total.
Communication (International Preliminary Report on Patentability) issued by the International Searching Authority in International Patent Application No. PCT/US2018/033880, dated Nov. 26, 2019, 7 pages total.

(Continued)

*Primary Examiner* — Quanglong N Truong

(74) *Attorney, Agent, or Firm* — Troutman Pepper

(57) ABSTRACT

The present invention provides fractionated polymer compositions that have antibacterial, antifungal and antiviral activity. These compositions are useful in the treatment infectious diseases caused by pathogens and for other uses.

15 Claims, 13 Drawing Sheets

(56) References Cited

OTHER PUBLICATIONS

Communication (International Search Report and Written Opinion) issued by the International Searching Authority in International Patent Application No. PCT/US2018/033880, dated Sep. 20, 2018, 11 pages total.

Communication (pursuant to Article 94(3) EPC) issued by the European Patent Office in European Patent Application No. 14884461.6, dated Jul. 19, 2019, 5 pages total.

Denton, G.W. (1991) Chlorhexidine. In: Block, S.S., Ed., Disinfction, Sterization, Preservations, 4 Edition, Lea & Fegiber, Philadelphia, 274-289.

European Extended Search Report Issued in European Patent Application No. 10822298.5 for PCT/RU2010/000292, dated Nov. 20, 2013, 3 pages.

European Extended Search Report Issued in European Patent Application No. 13853343.5 for PCT/RU2013/000394, dated Jun. 6, 2016, 6 pages.

Extended European Search Report Issued in European Application No. 16167120.1 dated Oct. 27, 2016, 6 pages.

Extended European Search Report Issued in European Patent Application No. 14884461.6, dated Aug. 2, 2017, 8 pages.

International Search Report and Written Opinion Issued in International Application No. PCT/RU2014/000917 dated Apr. 29, 2015 and English Language Translation Thereof, 7 pages.

International Search Report and Written Opinion Issued in International Application No. PCT/RU2015/000253, dated Sep. 10, 2015 and English Translation Thereof, 10 pages.

Lysytsya, Andriy et al., "The Antiviral Action of Polyhexamethylene Guanidine Derivatives", Journal of Life Sciences (2014), vol. 8, No. 1, pp. 22-26.

Translation of the International Preliminary Report on Patentability dated Apr. 11, 2012 from corresponding International Application No. PCT/RU2010/000292, 4 pages.

Translation of the International Preliminary Report on Patentability dated Sep. 13, 2016 from corresponding International Application No. PCT/RU2014/000917, 5 pages.

Translation of the International Search Report and Written Opinion of the International Searching Authority dated Oct. 28, 2010, from corresponding International Application No. PCT/RU2010/000292, 11 pages.

Wei, Dafu et al., "Structural characterization and antibacterial activity of oligoguanidine (polyhexamethylene guanidine hydrochloride)", Materials Science and Engineering C 29 (2009), pp. 1776-1780.

Communication (pursuant to Article 94(3) EPC) issued by the European Patent Office in European Patent Application No. 14884461.6, dated Mar. 31, 2020, 5 pages total.

Communication (pursuant to Article 94(3) EPC) issued by the European Patent Office in European Patent Application No. 15879124.4, dated Apr. 2, 2020, 4 pages total.

Communication (pursuant to Article 94(3) EPC) issued by the European Patent Office in European Patent Application No. 14884461.6, dated Oct. 21, 2020, 3 pages total.

* cited by examiner

FRACTIONATED ANTIMICROBIAL COMPOSITIONS AND USE THEREOF

CROSS-REFERENCE TO RELATED APPLICATIONS

This application is a U.S. National Phase of International Patent Application No. PCT/US2018/033880, filed on May 22, 2018, which published as WO 2018/217743 A1 on Nov. 29, 2018, and claims priority to U.S. Provisional Application No. 62/633,761, filed on Feb. 22, 2018, and U.S. Provisional Application No. 62/510,446, filed on May 24, 2017, all of which are herein incorporated by reference in their entireties.

FIELD OF THE INVENTION

The present invention provides fractionated polymer compositions that have antibacterial, antifungal and antiviral activity. These compositions are useful in the treatment infectious diseases caused by pathogens and for other uses.

BACKGROUND OF THE INVENTION

The fast evolution of drug resistant pathogens is an important public health issue. (Fidel, P. L, et al., *Clin. Microbiol. Rev.*, 1999, 12(1):80-96). New antimicrobial compounds to treat resistant infections are widely sought and several publications report effective classes of compounds. U.S. Publication No. 2017/0013838 discloses antiviral agents of formula:

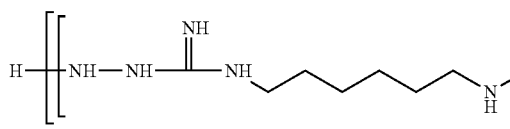

where HX is an acid, n is 3-20, and m is 4-20. Such compounds can be synthesized by ternary polycondensation of guanidine hydrochloride, with hexamethylene diamine and hydrazine hydrate.

International Publication No. WO 2016/118043 discloses hydrazine hemostatic agents of

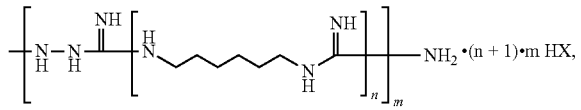

where n is 1-20, m is 1-10, and n×m is ≥8.

U.S. Pat. No. 8,993,712 discloses hydrazine compounds of formula:

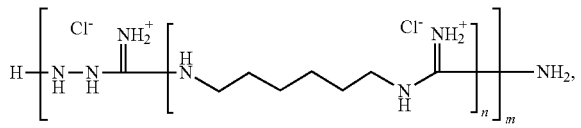

wherein n is 1-3, m is 2-10, z is 4-20, and X is absent or an acid. Such compounds exhibit strong antibacterial and antifungal properties.

New or improved agents which target resistant pathogens are continually needed that have low toxicity, enhanced antimicrobial activity, and other advantageous features. The compounds, compositions and methods described herein are directed towards these and other ends.

SUMMARY OF THE INVENTION

The present invention provides polymer fractions comprising Formula I, having an average molecular weight of from about 780 Da to about 5700 Da and a molecular distribution of less than about 10 kDa, Formula I having the structure:

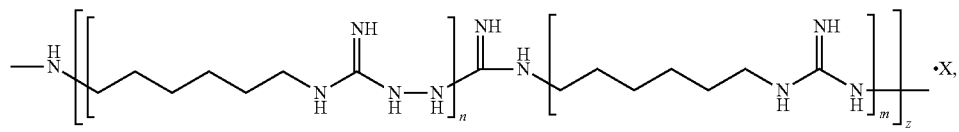

wherein constituent members are defined below.

The present invention further provides compositions comprising the Formula I polymer fractions and a pharmaceutically acceptable carrier.

The present invention further provides methods of preparing the Formula I polymer fractions of the invention, for example, by ternary polycondensation reaction of hexamethylenediamine, hydrazine hydrate and salts of guanidine and dialysis of the crude product to isolate specific Formula I fractions.

The present invention further provides methods of inhibiting growth of pathological agents (e.g., bacterial, fungal, viral, and protozoal agents) or cancer cells, comprising contacting the agent with an effective amount of the Formula I polymer fraction of the invention.

The present invention further provides a method of treating an infection in a subject in need thereof, comprising administering to the subject an effective amount of the Formula I polymer fraction of the invention.

The present invention further provides a method of treating cancer in a subject in need thereof, comprising administering to the subject an effective amount of the Formula I polymer fraction of the invention.

The present invention further provides a method for treating respiratory tract infections with the Formula I polymer fractions, in particular, lung infections (e.g., those infections caused by mixed bacterial and fungal strains) as well as Chronic Obstructive Pulmonary Disease (COPD), pneumonia, and Ventilator-associated pneumonia (VAP).

DETAILED DESCRIPTION

Figure 1:
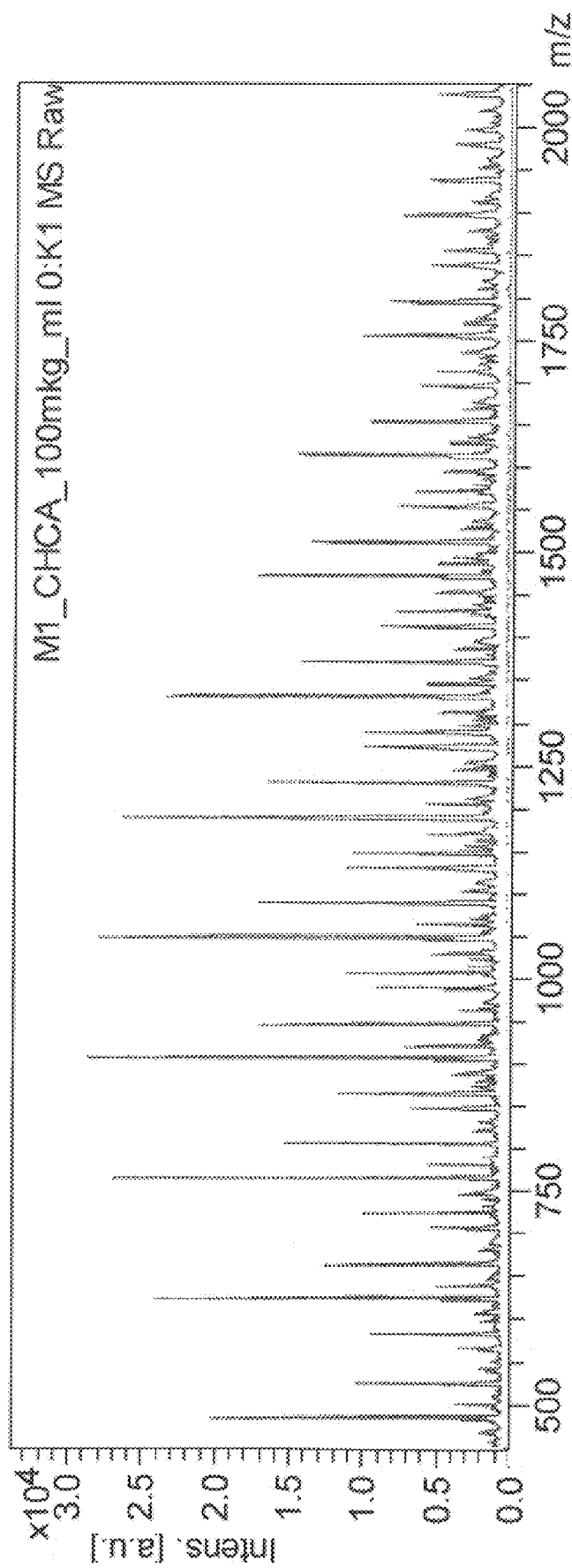
FIG. 1 is a mass spectrum of the compound preparation described in Example 1.

This invention provides, inter alia, biocidal preparations having high antimicrobial and antiviral activity and low toxicity. In particular, this invention provides a polymer fraction of Formula I:

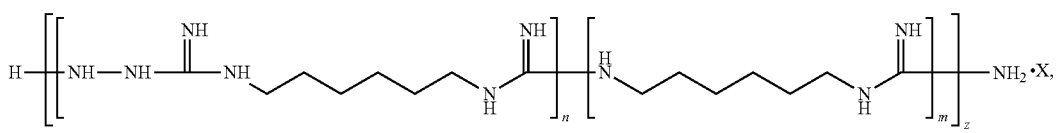

wherein: n is 1 to 3; m is 4 to 14; z is 1 to 6; and X is an acid.

Formula I can be produced by ternary polycondensation of hexamethylenediamine, hydrazine hydrate and salts of guanidine to form a product polymer which includes all products produced by the polymerization reaction. Applicants have surprisingly discovered that when the Formula I product polymer is separated into polymer fractions based on molecular weight and other parameters discussed, infra, the fractionated preparations exhibit advantageous properties, e.g., low toxicity and enhanced efficacy.

In some embodiments, the average molecular weight of the fractionated Formula I preparation is from about 780 Da to about 5700 Da.

In some embodiments, the average molecular weight values refer to the free-base form of the Formula I compounds (without the acid moiety). For example, in some embodiments, the average molecular weight of the free base form of the Formula I compounds (without the acid moiety) is from about 780 Da to about 5700 Da.

In some embodiments of the invention, the average molecular weight of the Formula I compounds (without the acid moiety) is less than about 3680 Da.

In some embodiments, the average molecular weight of the Formula I polymer fraction is about 1330±10% Da.

In some embodiments, the average molecular weight of the Formula I polymer fraction is about 1600±10% Da.

In some embodiments, the average molecular weight of the Formula I polymer fraction is about 1850±10% Da.

In some embodiments, the average molecular weight of the Formula I polymer fraction is about 2000±10% Da.

In some embodiments, the average molecular weight of the Formula I polymer fraction is about 2200±10% Da.

In some embodiments, the average molecular weight of the Formula I polymer fraction is about 2300±10% Da.

In some embodiments, the average molecular weight of the Formula I polymer fraction is about 2500±10% Da.

In some embodiments, the average molecular weight of the Formula I polymer fraction is about 2600±10% Da.

In some embodiments, the average molecular weight of the Formula I polymer fraction is about 2630±10% Da.

In some embodiments, the average molecular weight of the Formula I polymer fraction is about 2800±10% Da.

In some embodiments, the average molecular weight of the Formula I polymer fraction is about 3100±10% Da.

In some embodiments, the average molecular weight of the Formula I polymer fraction is about 3170±10% Da.

In some embodiments, the average molecular weight of the Formula I polymer fraction is about 3680±10% Da.

In some embodiments, the average molecular weight of the Formula I polymer fraction is about 5700±10% Da.

In some embodiments, the average molecular weight of the Formula I polymer fractions is about 910 Da to about 1200 Da.

In some further embodiments, the molecular distribution of the Formula I polymer fraction of the invention is less than about 10 kDa.

In some embodiments, the median molecular weight of the fractionated Formula I preparations is from about 1330 Da to about 3500 Da.

In some embodiments, the median molecular weight of the fractionated Formula I preparations is about 1330 Da, or about 1340 Da, or about 1350 Da, or about 1360 Da, or about 1370 Da, or about 1380 Da, or about 1390 Da, or about 1400 Da, or about 1410 Da, or about 1420 Da, or about 1430 Da, or about 1440 Da, or about 1450 Da, or about 1460 Da, or about 1470 Da, or about 1480 Da, or about 1490 Da, or about 1500 Da, or about 1550 Da, or about 1600 Da, or about 1650 Da, or about 1700 Da, or about 1750 Da, or about 1800 Da, or about 1850 Da, or about 1900 Da, or about 1950 Da, or about 2000 Da, or about 2500 Da, or about 3000 Da, or about 3100 Da, or about 3200 Da, or about 3300 Da, 3400 Da, 3500 Da.

In some embodiments, the polymer fraction is substantially purified, e.g., by dialysis such that it is substantially free of other polymer components falling outside of the specified molecular weight range. In some embodiments, the polymer fraction of Formula I is substantially isolated from the Formula I reaction product formulation.

The Formula I structure is modified with an acid "X" moiety which includes any acid addition salt, e.g., HCl, $H_2SO_4$, AcOH, $H_3PO_4$, $H_2CO_3$, or $C_6H_5COOH$.

In some embodiments, X is HCl.
In some embodiments, X is $H_2SO_4$.
In some embodiments, X is AcOH.

In some embodiments, n, m, and z represent average values of the constituent components in the fractionated polymer preparation.

In some embodiments, the ratio of n:m is 1:8.
In some embodiments, n is 1.
In some embodiments, n is 2.
In some embodiments n is 3.
In some embodiments m is 4.
In some embodiments, m is 5.
In some embodiments, m is 6.
In some embodiments, m is 7.
In some embodiments, m is 8.
In some embodiments, m is 9.
In some embodiments, m is 10.
In some embodiments, m is 11.
In some embodiments, m is 12.
In some embodiments, m is 13.
In some embodiments m is 14.

In some further embodiments, z is 1 to 6, or 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0.

In some embodiments, z is 1.
In some embodiments, z is 1.3.
In some embodiments, z is 1.4.
In some embodiments, z is 1.7.
In some embodiments, z is 1.8.
In some embodiments, z is 1.9.
In some embodiments, z is 2.0.
In some embodiments, z is 2.4.
In some embodiments, z is 2.8.
In some embodiments, z is 4.3.

In some embodiments, the Formula I polymer fraction is defined such that n is 1, m is 8, z is 1.4, and X is HCl, the average molecular weight is 1850 (±10%) Da and the molecular distribution less than about 3000 Da.

In some embodiments, the Formula I polymer fraction is defined such that n is 1, m is 8, z is 2.4, and X is HCl, the average molecular weight is 3170 (±10%) Da and the molecular distribution is less than about 10 000 Da.

In some embodiments, the Formula I polymer fraction is defined such that n is 1, m is 8, z is 1.8, and X is HCl, the average molecular weight is 2300 (±10%) Da and the molecular distribution is between about 1000 and about 3000 Da.

In some embodiments, the Formula I polymer fraction is defined such that n is 1, m is 8, z is 1.9, and X is HCl, the average molecular weight is 2500 (±10%) Da and the molecular distribution is between about 2000 and about 3000 Da.

In some embodiments, the Formula I polymer fraction is defined such that n is 1, m is 8, z is 2.8, and X is HCl, the average molecular weight is 3680 (±10%) Da and the molecular distribution is between about 3000 and about 5000 Da.

In some embodiments, the Formula I polymer fraction is defined such that n is 3, m is 4, z is 1.4, and X is HCl, the average molecular weight is 1600 (±10%) Da and the molecular weight distribution is less than about 3000 Da.

In some embodiments, the Formula I polymer fraction is defined such that n is 1, m is 14, z is 1.3, and X is HCl, the average molecular weight is 3170 (±10%) Da and the molecular distribution is less than about 10 000 Da.

In some embodiments, the Formula I polymer fraction is defined such that n is 1, m is 8, z is 1.7, and X is $H_2SO_4$, the average molecular weight is 2600 (±10%) Da and the molecular distribution is less than 10 000 Da.

In some embodiments, the Formula I polymer fraction is defined such that n is 1, m is 8, z is 1.7 and X is AcOH, the average molecular weight is 2200 (±10%) Da and the molecular distribution is less than about 3 000 Da.

In some embodiments, the Formula I polymer fraction is defined such that n is 1, m is 8, z is 1, and X is HCl, the average molecular weight is 1330 (±10%) Da and the molecular distribution is less than about 2 000 Da.

In some embodiments, the Formula I polymer fraction is defined such that n is 1, m is 8, z is 2.4, and X is HCl, the average molecular weight is 3100 (±10%) Da and the molecular distribution is less than about 5 000 Da.

In some embodiments, the Formula I polymer fraction is defined such that n is 1, m is 8, z is 4.3, and X is HCl, the average molecular weight is 5700 (±10%) Da and the molecular distribution is between about 5000 to about 10 000 Da.

In some embodiments, the Formula I polymer fraction is defined such that n is 1, m is 8, z is 2.0, and X is HCl, the average molecular weight 5700 (±10%) Da and the molecular distribution between about 2000 to about 10 000 Da.

Synthesis

Compounds and polymer fractions of the invention, including salts thereof, can be prepared using known organic synthesis techniques and can be synthesized according to any of numerous possible synthetic routes. For example, in some embodiments, the Formula I compounds are synthesized by ternary polycondensation reaction of hexamethylenediamine, hydrazine hydrate and salts of guanidine. Subsequent dialysis of the crude product can be performed to facilitate isolation of Formula I preparations having a narrow and precise molecular weight distribution. In the dialysis step, fractioning may include one or several steps of filtering and concentration with the use of an appropriate dialysis module selected by a person of ordinary skill in art.

In some embodiments, the invention provides a method of preparing the Formula I polymer fraction comprising:

reacting hexamethylenediamine with a guanidine salt and a compound selected from the group consisting of: hydrazine hydrate, semicarbazide, semicarbazide chlorhydrate, carbohydrazide, and aminoguanidine hydrochloride, at a temperature of 175° C. to 195° C.; and isolating the polymer fraction by dialysis.

In some embodiments, the hexamethylenediamine and guanidine salt are reacted with hydrazine hydrate to afford the Formula I polymerization product.

In some embodiments, the hexamethylenediamine and guanidine salt are reacted with semicarbazide to afford the Formula I polymerization product.

In some embodiments, the hexamethylenediamine and guanidine salt are reacted with semicarbazide chlorhydrate to afford the Formula I polymerization product.

In some embodiments, the hexamethylenediamine and guanidine salt are reacted with carbohydrazide.

In some embodiments, the hexamethylenediamine and guanidine salt are reacted with aminoguanidine hydrochloride to afford the Formula I polymerization product.

In some embodiments, the invention provides a Formula I polymer fraction having an average molecular weight of from about 1330 Da to about 5700 Da and a molecular distribution of less than about 10 kDa, Formula I having the structure:

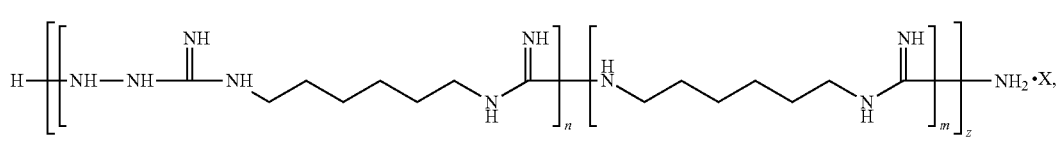

wherein n is 1-3; m is 4-14; z is 1-6; and X is an acid, the polymer fraction being prepared by a process comprising reacting hexamethylenediamine with a guanidine salt and a compound selected from the group consisting of: hydrazine hydrate, semicarbazide, semicarbazide chlorhydrate, carbohydrazide, and aminoguanidine hydrochloride, at a temperature of 175° C. to 195° C.; and isolating the polymer fraction by dialysis.

In some embodiments of the invention, the Formula I compounds are prepared using the following reagents and mol % ratios:

| Reagent | Mol % |
| --- | --- |
| guanidine salt | 50.0 |
| hexamethylenediamine | 31.25-46.87 |
| hydrazine hydrate | 3.13-18.75 (to 100%)* |
| water | 0-20 |

*In some embodiments, the mole % of hexamethylenediamine + hydrazine is equal to the mole % of guanidine. The total mol % of all three components is taken as 100%.

In some embodiments of the invention, the Formula I compounds are prepared using the following reagents and mol % ratios:

| Reagent | Mol % |
| --- | --- |
| guanidine salt | 50.0 |
| hexamethylenediamine | 31.25-46.87 |
| semicarbazide | 3.13-18.75 (to 100%)* |
| water | 0-20 |

*In some embodiments, the mole % of hexamethylenediamine + hydrazine is equal to the mole % of guanidine. The total mol % of all three components is taken as 100%.

In some embodiments of the invention, the Formula I compounds are prepared using the following reagents and mol % ratios:

| Reagent | Mol % |
| --- | --- |
| guanidine salt | 50.0 |
| hexamethylenediamine | 31.25-46.87 |
| semicarbazide chlorhydrate | 3.13-18.75 (to 100%)* |
| water | 0-20 |

*In some embodiments, the mole % of hexamethylenediamine + hydrazine is equal to the mole % of guanidine. The total mol % of all three components is taken as 100%.

In some embodiments of the invention, the Formula I compounds are prepared using the following reagents and mol % ratios:

| Reagent | Mol % |
| --- | --- |
| guanidine salt | 50.0 |
| hexamethylenediamine | 31.25-46.87 |
| carbohydrazide | 1.57-9.37 (to 100%)* |
| water | 0-50 |

*In some embodiments, the mole % of hexamethylenediamine + hydrazine is equal to the mole % of guanidine. The total mol % of all three components is taken as 100%.

In some embodiments of the invention, the Formula I compounds are prepared using the following reagents and mol % ratios:

| Reagent | Mol % |
| --- | --- |
| guanidine salt | 50.0 |
| hexamethylenediamine | 31.25-46.87 |
| aminoguanidine hydrochloride | 3.13-18.75 (to 100%)* |
| water | 0-20 |

*In some embodiments, the mole % of hexamethylenediamine + hydrazine is equal to the mole % of guanidine. The total mol % of all three components is taken as 100%.

Methods

The compounds and polymer fractions of the invention have antimicrobial activity and can inhibit the growth of one or more pathogenic and/or infectious agents. Accordingly, the compounds and polymer fractions of the invention can be used to inhibit growth of an agent by contacting the agent with one or more of the compounds and/or polymer fractions described herein. In some embodiments, the compounds and polymer fractions can act to inhibit the growth and/or activity of bacterial, fungal, viral, protozoal agents or cancer cells. In further embodiments, the compounds of the invention can be used to treat an infection in an individual or subject in need of treatment by administering an effective amount of a compound or polymer fraction of the invention. In further embodiments, the compounds or polymer fractions of the invention can be used to treat cancer in an individual or subject in need of such treatment by administering and effective amount of a compound or polymer fraction of the invention.

Agents to which the present compounds and polymer fractions inhibit and/or modulate include any agent capable of causing infection or disease. In some embodiments, the compounds of the invention can be selective. By "selective" is meant that the compound or polymer fractions binds to or inhibits a particular agent with greater affinity or potency, respectively, compared to at least one other compound or polymer fraction.

Another aspect of the present invention pertains to methods of treating and/or preventing an infectious disease or disorder in an individual (e.g., patient) by administering to the individual in need of such treatment a therapeutically effective amount or dose of a compound or polymer fraction of the present invention or a pharmaceutical composition thereof. An infectious disease can include any disease, disorder or condition that is directly or indirectly linked to activity of a pathogen. An infectious disease can also include any disease, disorder or condition that can be prevented, ameliorated, or cured by modulating growth of a pathogenic agent such as bacterial, fungal, viral, and protozoal agents.

In some embodiments, the infection is a mixed infection.

In some embodiments, the infection is a systemic infection.

In some embodiments, the infection is a dental infection.

In some embodiments, the infection is a skin and soft tissue infection or an infection of a wound/ulcers.

In some embodiments, the infection is a mucosal infection.

In some embodiments, the infection is a respiratory tract infection.

In some embodiments, the infection is a lung infection, including, lung infections caused by mixed bacterial, fungal and/or viral strains. In some embodiments, the lung infection is Chronic Obstructive Pulmonary Disease (COPD), pneumonia, Ventilator-associated pneumonia (VAP), lung infection in cystic fibrosis patients, or fungal pneumonia. The invention also relates to prevention of certain diseases, including those diseases set forth herein, e.g., prevention of fungal pneumonia in immune-compromised patients. In some embodiments, the infection is a skin and/or soft tissue infection.

In some embodiments, the infection is an infection of abscesses.

In some embodiments, the infection is a sinusitis.

In some embodiments, the infection is a dental infection.

In some embodiments, the infection is an ophthalmologic infection.

In some embodiments, the invention is useful for treating a tumor.

In some embodiment, the invention is useful for treating and/or preventing a viral respiratory tract infection.

In some embodiments, the invention is useful for treating and/or preventing a urinary tract infection.

In some embodiments, the invention is useful for treating and/or preventing cystitis.

In some embodiments, the invention is useful for treating and/or preventing otitis.

In some embodiments, the invention is useful for treating and/or preventing peritonitis and intra-abdominal sepsis.

In some embodiments, the invention is useful for treating and/or preventing pleural empyema.

In some embodiments, the invention is useful for treating and/or preventing sepsis.

In some embodiments, the invention is useful for treating and/or preventing an IBD, Crohn's diseases, and/or Clostridial infection.

In some embodiments, the invention is useful for treating and/or preventing infections caused by multi-drug resistant bacteria, virus or fungi.

In some embodiments, the invention is useful for treating and/or preventing infections caused by vancomycin-resistant *S. aureus* (VRSA).

In some embodiments, the invention is useful for treating and/or preventing infections caused by *Burkholderia cepacia* bacteria.

In some embodiments, the invention is useful for treating and/or preventing the growth of microbial biofilms.

In some embodiments, the invention is useful for the treatment of surfaces, e.g., surfaces found in nature (e.g., ponds).

Formulations and Dosage Forms

When employed as a medicinal or pharmaceutical agent, the Formula I preparations described herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, preparations of Formula I in combination with one or more pharmaceutically acceptable carriers (excipients). In making the compositions of the invention, the active ingredient is typically mixed with an excipient, diluted by an excipient or enclosed within such a carrier in the form of, for example, an aqueous solution, or a capsule, sachet, paper, or other container. When the excipient serves as a diluent, it can be a solid, semi-solid, or liquid material, which acts as a vehicle, carrier or medium for the active ingredient. Thus, the compositions can be in the form of suspensions, emulsions, solutions, syrups, aerosols (as a solid or in a liquid medium), tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The liquid forms in which the compounds and compositions of the present invention can be incorporated for administration topically, orally or by injection include aqueous solutions, suitably flavored syrups, aqueous or oil suspensions, and emulsions, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

In some embodiments, Formula I and/or polymer fractions thereof are administered locally.

In some embodiments, Formula I and/or polymer fractions thereof are administered by instillation.

In some embodiments, Formula I and/or polymer fractions thereof are administered topically.

In some embodiments, Formula I and/or polymer fractions thereof are administered enterally.

In some embodiments, Formula I and/or polymer fractions thereof are administered parenterally.

In some embodiments, the compounds and polymer fractions of the invention are administered in combination with at least one other compound or component that potentiates the activity of the antimicrobial agent. When being used to treat cancer and/or tumor growth, the compounds and polymer fractions may be administered in combination with other antimicrobial or anticancer drugs.

In some embodiments, Formula I and/or polymer fractions of the invention are prepared in solution form for inhalation.

In some embodiments, Formula I and/or polymer fractions thereof are prepared in powder form for inhalation.

In some embodiments, Formula I and/or polymer fractions thereof are for treating lung infections in cystic fibrosis, chronic obstructive pulmonary disease, bronchiectasis, lung transplantation, fungal pneumonia, ventilator-associated pneumonia, and the like.

In some embodiments, Formula I and/or polymer fractions thereof are prepared in solution for instillation. Such solutions are useful, for example, for treatment of urinary tract infections, sinusitis, abscesses, peritonitis, and lung empyema.

In some embodiments, Formula I and/or polymer fractions thereof are prepared in solution form, e.g., for dental applications e.g., treatment of root canals, compositions to be applied to periodontal pockets, and oral rinse solutions and the like.

Topical preparations of Formula I and/or polymer fractions thereof may be used for a variety of applications, e.g., treatment of ulcers, burns, and for impregnation of materials.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like. The therapeutic dosage of the compounds and polymer fractions of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds and polymer fractions of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Reagents and solvents used below can be obtained from commercial sources such as Sigma-Aldrich. Mass spectrometry results are reported as the ratio of mass over charge, followed by relative abundance of each ion (in parenthesis). In tables, a single m/e value is reported for the M+H (or, as noted, M−H) ion containing the most common atomic isotopes.

The following are examples of compounds and polymer fractions of the invention.

Example 1

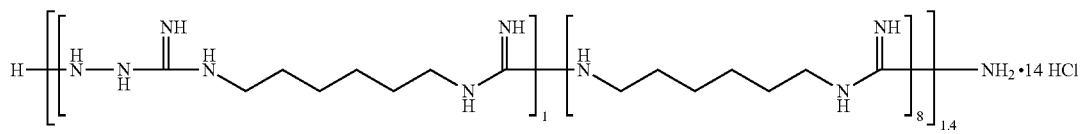

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 1 h at 175-180° C. The temperature was then raised to 190° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper cutoff of 3 kDa, and 1250 mL of filtrate was obtained containing 120 g of the title compound of Example 1. An average molecular weight of 1850 (±10%) Da was determined for the title compound (in its free base form without the acid) by acid-base titration of the residual terminal amino groups.

The Example 1 compound was examined by MALDI-MS. 0.1 ml of an aqueous solution of α-cyano-4-hydroxycinnamic acid (CHCA) was added to 0.1 ml of a 0.1 mg/ml aqueous solution of the Example 1 preparation and mixed. 1 µl of the resulting solution was applied onto the target for MALDI and air dried. The resulting sample was examined on a MALDI-TOF device (Brucker Daltonics) using a laser operating frequency of 400 nm. Mass ions were registered in the positive ions mode in the range of m/z 480-2000 Da. The mass spectrum for the Example 1 preparation is shown in FIG. 1.

Alternate Synthesis A:

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and semicarbazide (7.5 g, 0.1 mol). The outlet tube was connected to the receiver to capture ammonia. The flask contents were stirred and heated to 175-180° C. with gradual removal of water and ammonia over 2 h at 175-180° C. The temperature was then raised to 190° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper weight cutoff of 3 kDa, and 1250 mL of filtrate was obtained containing 120 g of the title compound of Example 1.

Alternate Synthesis B:

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and semicarbazide chlorhydrate (11.05 g, 0.1 mol). The outlet tube was connected to the receiver to capture ammonia. The flask contents were stirred and heated to 175-180° C. with gradual removal of water and ammonia over 2 h at 175-180° C. The temperature was then raised to 190° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper weight cutoff of 3 kDa, and 1250 mL of filtrate was obtained containing 120 g of the title compound of Example 1.

Alternate Synthesis C:

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and semicarbazide chlorhydrate (11.05 g, 0.1 mol) and water (5 mL). The outlet tube was connected to the receiver to capture ammonia. The flask contents were stirred and heated to 175-180° C. with gradual removal of water and ammonia over 2 h at 175-180° C. The temperature was then raised to 190° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper weight cutoff of 3 kDa, and 1250 mL of filtrate was obtained containing 120 g of the title compound of Example 1.

Alternate Synthesis D:

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and carbohydrazide (90 g, 0.1 mol). The outlet tube was connected to the receiver to capture ammonia. The flask contents were stirred and heated to 175-180° C. with gradual removal of water and ammonia over 2 h at 175-180° C. The temperature was then raised to 190° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper weight cutoff of 3 kDa, and 1250 mL of filtrate was obtained containing 120 g of the title compound of Example 1.

Alternate Synthesis E:

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and aminoguanidine hydrochloride (110.5 g, 0.1 mol). The outlet tube was connected to the receiver to capture ammonia. The flask contents were stirred and heated to 175-180° C. with gradual removal of water and ammonia over 2 h at 175-180° C. The temperature was then raised to 190° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper weight cutoff of 3 kDa, and 1250 mL of filtrate was obtained containing 120 g of the title compound of Example 1.

Example 2

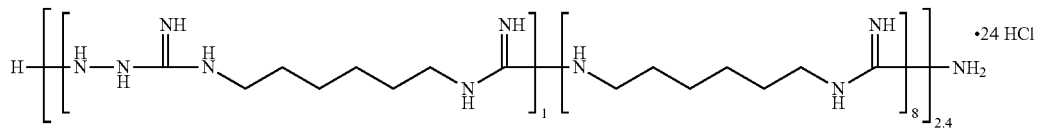

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 2 h at 175-180° C. The temperature was then raised to 195° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper cutoff of 10 kDa, and 1350 mL of filtrate was obtained containing 130 g of the title compound of Example 2. An average molecular weight of 3170 (±10%) Da was determined for the title compound (in its free base form without the acid) by acid-base titration of the residual terminal amino groups.

Example 3

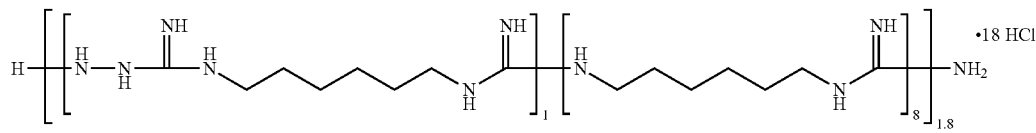

The title compound was prepared using the method set forth in Example 1. In this example, 600 mL of the resulting filtrate (oligomer solution with an upper weight cutoff of 3000 Da) was diluted with water to 5.9 L, and subjected to dialysis on a filter membrane module with a membrane having an upper weight cutoff of 1000 Da to separate 5.4 L of filtrate. The remaining dialysate was separated to give 450 mL of a solution containing 44 g of the title compound of Example 3. An average molecular weight of 2300 D was determined for the title compound (in its free-base form without the acid).

Example 4

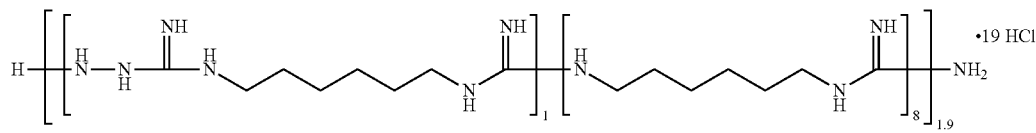

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 1 h at 175-180° C. The temperature was then raised to 190° C. and the flask contents were stirred for 4 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper cutoff of 3 kDa, and 1300 mL of filtrate was obtained containing 110 g of a non-volatile substance. 600 mL of this filtrate was diluted with water to 5 L and subjected to dialysis on a filter membrane module with a membrane having an upper weight cutoff of 2 kDa to separate 4.7 L of a filtrate. The remaining dialysate was separated to give 290 mL of a solution containing 28 g of the title compound of Example 4. An average molecular weight of 2500 (±10%) Da was determined for the title compound (in its free base form without the acid).

Example 5

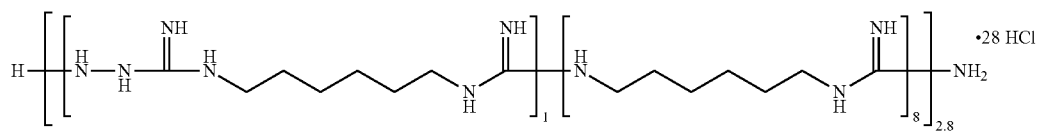

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 2 h at 175-180° C. The temperature was then raised to 195° C. and the flask contents were stirred for 1.5 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper cutoff of 5 kDa, and 1230 mL of filtrate was obtained containing 120 g of the oligomer with the upper weight cutoff of 5 kDa. 600 mL of this filtrate was diluted with water to 6 L and subjected to dialysis on a filter membrane module with a membrane having an upper weight cutoff of 3 kDa to separate 5.6 L of a filtrate. The remaining dialysate was separated to give 360 mL of a solution containing 35 g of the title compound of Example 5. An average molecular weight of 3680 (±10%) Da was determined for the title compound (in its free base form without the acid).

Example 6

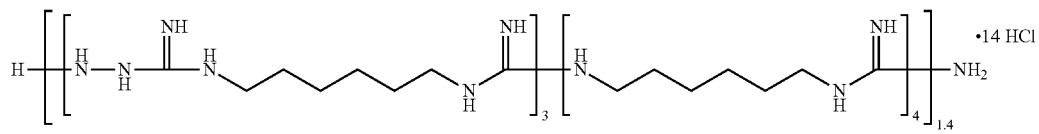

The title compound was prepared using the method set forth in Example 1 using the following reagents:

| Reagent | Mol |
|---|---|
| Guanidine hydrochloride | 1.0 |
| Hexamethylenediamine | 0.66 |
| Hydrazine hydrate | 0.33 |

The title compound of Example 6 was obtained as a 10% water solution. The average molecular weight of the title compound (in its free base form without the acid) was 1600 (±10%) Da, as determined by acid-base titration of the residual terminal amino groups.

Example 7

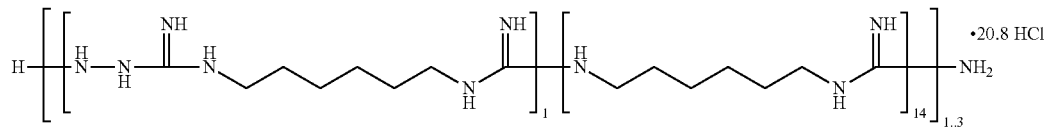

The title compound was prepared using the method set forth in Example 2 using the following reagents:

| Reagent | Mol |
|---|---|
| Guanidine hydrochloride | 1.0 |
| Hexamethylenediamine | 0.9375 |
| Hydrazine hydrate | 0.0625 |

The title compound of Example 7 was obtained as a 10% water solution. The average molecular weight of the title compound (in its free base form without the acid) was 2800 (±10%) Da, as determined by acid-base titration of the residual terminal amino groups.

Example 8

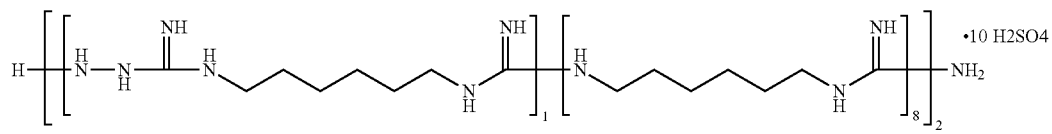

The title compound was prepared using the method set forth in Example 2 using the following reagents:

| Reagent | Mol |
|---|---|
| Guanidine sulfate | 1.0 |
| Hexamethylenediamine | 0.9 |
| Hydrazine hydrate | 0.1 |

The title compound of Example 8 was obtained as a 10% water solution. The average molecular weight of the title compound (in its free base form without the acid) was 2600 (±10%) Da, as determined by acid-base titration of the residual terminal amino groups.

Example 9

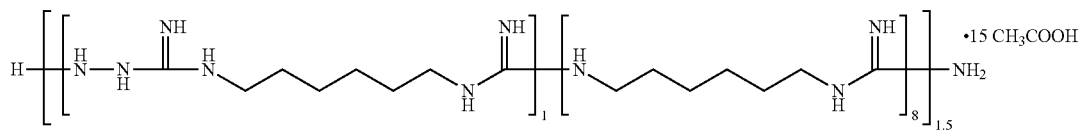

The title compound was prepared using the method set forth in Example 1 using the following reagents:

| Reagent | Mol |
|---|---|
| Guanidine acetate | 1.0 |
| Hexamethylenediamine | 0.9 |
| Hydrazine hydrate | 0.1 |

The title compound of Example 9 was obtained as a 10% water solution. The average molecular weight of the title compound (in its free base form without the acid) was 2000 (±10%) Da, as determined by acid-base titration of the residual terminal amino groups.

Example 10

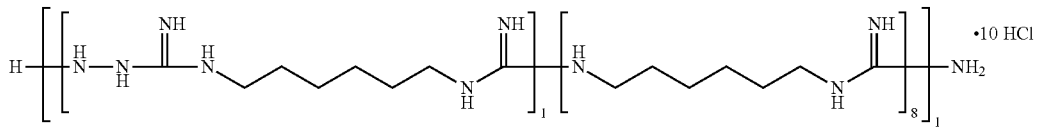

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 1 h at 175-180° C. The temperature was then raised to 190° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper cutoff of 2 kDa, and 1000 mL of filtrate was obtained containing 80 g of the title compound of Example 10. An average molecular weight of 1330 (±10%) Da was determined for the title compound (in its free base form without the acid) by acid-base titration of the residual terminal amino groups.

Example 11

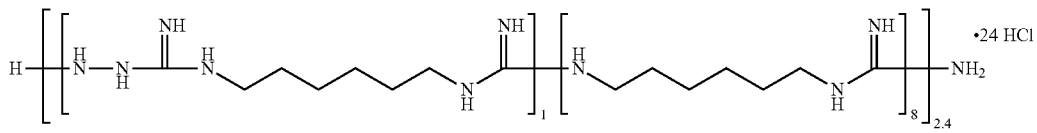

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 2 h at 175-180° C. The temperature was then raised to 195° C. and the flask contents were stirred for 1 h. The warm reaction mass was cooled to 130-140° C., hot water (150 mL) was added with stirring, and the mixture was left to stir until complete dissolution of the reaction mass was achieved. The resulting solution was decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper cutoff of 5 kDa, and 1300 mL of a solution containing 126 g title compound of Example 11. An average molecular weight of 3100 (±10%) Da was determined for the title compound (in its free base form without the acid) by acid-base titration of the residual terminal amino groups.

Example 12

Water (1200 mL) was added to 300 mL of the resulting 50% oligomer solution to afford a 10% solution of the crude product. The solution was then filtered through a membrane module with an upper cutoff of 10 kDa, and 1350 mL of a solution containing 1270 g of a non-volatile substance. 600 mL of this filtrate was diluted with water to 6 L and subjected to dialysis on a filter membrane module with a membrane having an upper weight cutoff of 5 kDa to separate 5.8 L of a filtrate. The remaining dialysate was separated to give 180 mL of a solution containing 9 g of the target title compound of Example 12. An average molecular weight of 5700 (±10%) Da was determined for the title compound (in its free base form without the acid).

Example 13

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 2 h and then increased temperature at 195° C. and mixed for an hour. The temperature was then raised to 195° C. and the flask contents were stirred for 2 h. The warm reaction mass was cooled to 130-140° C., hot water (150 mL) was added with stirring, and the mixture was left to stir until complete dissolution of the reaction mass was achieved. The resulting solution was

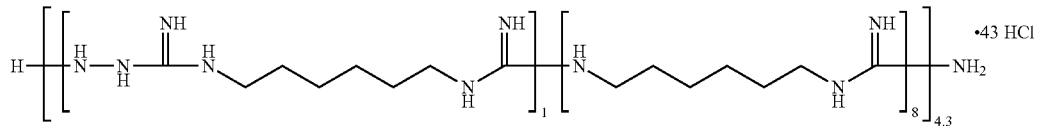

A heat-resistant 1-L flask equipped with a gas outlet tube, a stir bar and a thermometer was charged with guanidine hydrochloride (95.5 g, 1.0 mol, 48.7 wt. %), hexamethylenediamine (104.4 g, 0.9 mol, 48.7 wt. %) and hydrazine hydrate (5.0 g, 0.1 mol, 2.6 wt. %). The outlet tube was connected to the receiver to capture ammonia. The flask contents were stirred and heated to 175-180° C. with gradual removal of water and ammonia over 2 h at 175-180° C. The temperature was then raised to 195° C. and the flask contents were stirred for 2 h. The warm reaction mass was cooled to 130-140° C., hot water (150 mL) was added with stirring, and the mixture was left to stir until complete dissolution of the reaction mass was achieved. The resulting solution was then poured out and the flask was rinsed with water (30 mL) and both solutions were combined. The combined solution was neutralized with acid to pH 6-7, and 330 mL of the oligomer water solution having a concentration of 50% was obtained as a clear, substantially colorless liquid.

decanted and the flask was rinsed with water (30 mL) and then recombined with the decanted solution. The combined solution was neutralized with acid to pH 6-7, and 330 mL of the oligomer water solution having a concentration of 50% was obtained as a clear, substantially colorless liquid.

Water (1200 mL) was added to 300 mL of the resulting 50% oligomer solution to afford a 10% solution of the crude product. The solution was then filtered through a membrane module with an upper cutoff of 10 kDa, and 1350 mL of a solution containing 1270 g of a non-volatile substance. 600 mL of this filtrate was diluted with water to 6 L and subjected to dialysis on a filter membrane module with a membrane having an upper weight cutoff of 2 kDa to separate 5.7 L of a filtrate. The remaining dialysate was separated to give 290 mL of a solution containing 28 g of the target title compound with formula

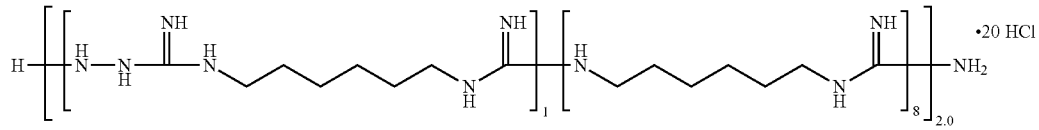

An average molecular weight of 2630 (±10%) Da was determined for the title compound (in its free base form without the acid).

Example 14

Structural characteristics of the preparations isolated in Examples 1-13 are shown in Table 1. Elemental analysis of the Example 1-12 preparations (based on dry matter) are shown in Table 2.

TABLE 1

| Example No. | Acid | n | m | z | Average MW (±10% Da) | Weight range limits, Da |
|---|---|---|---|---|---|---|
| 1 | HCl | 1 | 8 | 1.4 | 1850 | up to 3000 |
| 2 | HCl | 1 | 8 | 2.4 | 3170 | up to 10 000 |
| 3 | HCl | 1 | 8 | 1.8 | 2300 | 1000-3000 |
| 4 | HCl | 1 | 8 | 1.9 | 2500 | 2000-3000 |
| 5 | HCl | 1 | 8 | 2.8 | 3680 | 3000-5000 |
| 6 | HCl | 3 | 4 | 1.4 | 1600 | up to 3000 |
| 7 | HCl | 1 | 14 | 1.3 | 2800 | up to 10 000 |
| 8 | $H_2SO_4$ | 1 | 8 | 2.0 | 2600 | up to 10 000 |
| 9 | AcOH | 1 | 8 | 1.5 | 2000 | up to 3000 |
| 10 | HCl | 1 | 8 | 1 | 1330 | up to 2000 |
| 11 | HCl | 1 | 8 | 2.4 | 3100 | up to 5000 |
| 12 | HCl | 1 | 8 | 4.3 | 5700 | 5000-10 000 |
| 13 | HCl | 1 | 8 | 2.0 | 2630 | 2000-10 000 |

TABLE 2

| Example No. | Elemental analysis data, % | | | |
|---|---|---|---|---|
| | C | H | N | Cl(S) |
| 1 | 44.76 | 8.84 | 25.43 | 20.97 |
| 2 | 44.88 | 8.82 | 25.29 | 21.02 |
| 3 | 44.84 | 8.83 | 25.36 | 20.95 |
| 4 | 44.86 | 8.77 | 25.23 | 20.85 |
| 5 | 44.93 | 8.80 | 25.23 | 21.05 |
| 6 | 40.49 | 8.24 | 28.16 | 23.06 |
| 7 | 46.31 | 9.05 | 25.04 | 19.42 |
| 8 | 41.65 | 8.19 | 23.52 | 8.69 |
| 9 | 51.61 | 9.34 | 22.20 | — |
| 10 | 44.60 | 8.89 | 25.65 | 20.90 |
| 11 | 44.94 | 8.83 | 25.21 | 21.02 |
| 12 | 44.99 | 8.84 | 25.19 | 20.98 |
| 13 | 44.87 | 8.83 | 25.33 | 20.96 |

A comparison of the biocidal activity of Examples 1-12 and a prototype preparation described in U.S. Pat. No. 8,993,712 (having an average molecular weight of 5273 to 26000 Da) is shown in the following examples. The prototype preparation is a compound of formula:

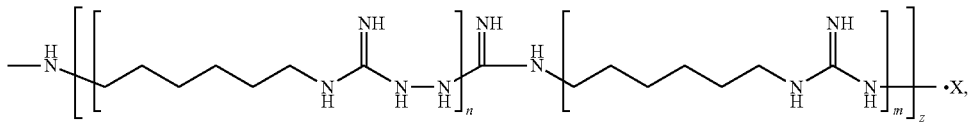

wherein n=1 to 3; m=2-10; z=4-20; and X is absent or an acid, having an average ratio of n/m of 1/9, a polymerization degree of 40 and higher and an average weight of the polymer molecule (without the counterion) ranging from about 5273 Da to about 26000 Da.

Example 15

In this example the efficacy of the Example 1-12 preparations was tested against various bacteria (aerobic and anaerobic) and fungal pathogens.

| | |
|---|---|
| Bacteria tested: | *Escherichia coli* ATCC 25922, *Pseudomonas aeruginosa* ATCC27853, *Fusobacterium nucleatum* VT13-23, *Staphylococcus aureus* VT 10-209, *Mycobacterium tuberculosis* H37Rv |
| Fungi tested: | *Candida albicans* VT10-14, *Candida glabrata* VT14 to 140, *Fusarium moniliforme* VT1147, *Aspergillis fumigatus* ATCC 20430 |
| Culture Media: | For bacterial cultivation: Mueller-Hinton broth, Mueller-Hinton agar, Schedler broth, Schedler agar, Columbia agar, *Brucella* agar and Trypticase Soy Agar. For fungal cultivation: Saburo broth and agar (bioMérieux, France) |

Antimicrobial activity was evaluated by a serial dilution method. Compounds were dissolved in sterile water and used in concentrations of 500 to 0.0025 mg/L. The drug concentrations in the medium in adjacent test tubes differed twice. Experimental results were collected after 72-hour cultivation of bacteria at 37° C. Data are shown in Table 3.

TABLE 3

Antibacterial Activity.

| Example No. | Acid | Weight range limits, Da | S. aureus ATCC | E. coli ATCC9223 | F. nucleatum | P. aeruginosa ATCC27853 | M. tuberculosis H37Rv |
|---|---|---|---|---|---|---|---|
| 1 | HCl | up to 3000 | 0.03 (2) | 3.1 (7) | 0.6-1.2 (3) | 0.07 (1) | 0.06 (6) |
| 2 | HCl | up to 10 000 | 0.12 | 0.3 (1) | 0.3 | 0.7 | 0.03 |
| 3 | HCl | 1000-3000 | 0.03 (2) | 3.1 (7) | 0.6-1.2 (3) | 0.07 (1) | 106 (6) |
| 4 | HCl | 2000-3000 | 0.12 (6) | 0.7-1.5 (4) | 0.3 (1) | 0.15-0.3 (5) | 0.015-0.03 (2) |
| 5 | HCl | 3000-5000 | 0.06 (3) | 0.7 (3) | 0.6 (4) | 0.07 (2) | 0.12 (7) |
| 6 | HCl | up to 3000 | 0.6 | 12.4 | 2.4 | 0.6 | 0.48 |
| 7 | HCl | up to 10 000 | 0.48 | 1.2 | 1.2 | 2.8 | 0.24 |
| 8 | H2SO4 | up to 10 000 | 0.48 | 1.2 | 2.4 | 4.1 | 1.2 |
| 9 | AcOH | up to 3000 | 0.6 | 2.4 | 2.4 | 1.2 | 1.2 (6) |
| 10 | HCl | up to 2000 | 0.06-0.12 (4) | 6.2 (8) | 0.6 (2) | 0.07-0.15 (3) | 0.12 (8) |
| 11 | HCl | up to 5000 | 0.015-0.03 (1) | 1.5-3.1 (6) | 0.6 (5) | 0.15 (6) | 0.03 (3) |
| 12 | HCl | 5000-10 000 | 0.12-0.25 (9) | 1.5 | 0.6-1.2 (5) | 0.15 (8) | 0.015 (1) |
| 13 | HCl | 2000-10 000 | 0.12 | 0.7 | 1.2 | 28 | 0.06 |
| Prototype | | | 0.25 | 0.7 (2) | 0.3 | 0.7 | 2.4 |

These data indicate that the compounds of the invention have a pronounced antibacterial activity.

TABLE 4

Antifungal activity.

| Example No. | Acid | Weight range limits, Da | C. albicans ATCC 14053 | A. fumigatus ATCC 204305 | F. moniliformes VT 1147 |
|---|---|---|---|---|---|
| 1 | HCl | up to 3000 | 0.6-1.2 (3) | 0.07 (1) | 0.9 |
| 2 | HCl | up to 10 000 | 0.3 | 0.7 | 2.5 |
| 3 | HCl | 1000-3000 | 0.6-1.2 (3) | 0.07 (1) | 1.2 |
| 4 | HCl | 2000-3000 | 0.3 (1) | 0.15-0.3 (5) | 5.4 |
| 5 | HCl | 3000-5000 | 0.6 (4) | 0.07 (2) | 4.0 |
| 6 to 05 | HCl | up to 3000 | 2.4 | 0.6 | 1.2 |
| 7 | HCl | up to 10 000 | 1.2 | 2.8 | 5.4 |
| 8 | H2SO4 | up to 10 000 | 2.4 | 4.2 | 0.9 |
| 9 | AcOH | up to 3000 | 2.4 | 1.2 | 4.0 |
| 10 | HCl | up to 2000 | 0.6 (2) | 0.07-0.15 (3) | 1.8 |
| 11 | HCl | up to 5000 | 0.6 (5) | 0.15 (6) | 4.0 |
| 12 | HCl | 5000-10 000 | 0.6-1.2 (5) | 0.15 (8) | 1.8 |
| 13 | HCl | 2000-10 000 | 0.6-1.2 | 0.15 | 1.8 |
| Prototype | | | 0.3 | 0.7 | 0.9 |

These data indicate that the compounds of the invention have a pronounced antifungal activity.

Example 16

In this example, the antiviral activity of compounds of the invention were tested.

| | |
|---|---|
| Viruses tested: | RNA-containing poliovirus, DNA-containing adenovirus, DNA-containing herpes simplex virus, RNA-containing hepatitis C virus, RNA-containing human immunodeficiency virus, RNA-containing influenza A virus. |
| Cell Culture: | Continuous culture of green monkey kidney Vero cells, human cells HeLa, porcine embryo kidney cells (PEKC), human lymphoblastoid MT-4 cells, canine kidney cells (MDCK). |

5.0% water solutions of the Example 1-12 preparations were prepared. The time of the virus contact with the agent was 0.5-1.0 minutes at the temperature of 20±2° C. Viral reproduction in cells was evaluated by virus-induced cytopathic effect determined by the degree of inhibiting infectious virus titer, measured as EC50. Data are shown in Table 5.

TABLE 5

Antiviral activity

| Example No. | Acid | Weight range limits, Da | EC50 | | | | | | |
|---|---|---|---|---|---|---|---|---|---|
| | | | Adeno-virus | Immuno-deficiency virus | Herpes virus (HSV1) | Poliomyelitis virus | Influenza A virus | Immuno-deficiency virus | Hepatitis C virus |
| 1 | HCl | up to 3000 | 0.8 | 0.5 | 0.12 | 0.9 | 0.25 | 0.3 | 0.15 |
| 2 | HCl | up to 10 000 | 3.5 | 2.0 | 0.48 | 0.45 | 4.0 | 0.9 | 1.0 |
| 3 | HCl | 1000-3000 | 0.2 | 1.0 | 0.06 | 1.8 | 0.5 | 0.6 | 0.6 |
| 4 | HCl | 2000-3000 | 1.6 | 3.5 | 0.28 | 1.8 | 4.0 | 1.8 | 0.6 |
| 5 | HCl | 3000-5000 | 3.5 | 3.5 | 0.48 | 3.6 | 2.0 | 3.6 | 1.6 |
| 6 to 05 | HCl | up to 3000 | 1.8 | 3.0 | 0.48 | 1.8 | 4.0 | 0.6 | 0.3 |
| 7 | HCl | up to 10 000 | 7.0 | 5.0 | 1.8 | 3.6 | 4.0 | 4.0 | 1.2 |
| 8 | $H_2SO_4$ | up to 10 000 | 4.0 | 7.2 | 3.6 | 7.2 | 8.0 | 8.0 | 2.4 |
| 9 | AcOH | up to 3000 | 1.6 | 5.0 | 0.24 | 1.8 | 1.0 | 0.6 | 0.6 |
| 10 | HCl | up to 2000 | 1.8 | 1.7 | 0.06 | 0.9 | 0.12 | 0.6 | 0.3 |
| 11 | HCl | up to 5000 | 0..4 | 3.5 | 0.24 | 1.8 | 1.0 | 0.6 | 0.6 |
| 12 | HCl | 5000 to 10 000 | 4.0 | 3.5 | 0.48 | 1.8 | 2.0 | 1.8 | 1.2 |
| 13 | HCl | 2000 to 10 000 | 2.0 | 7/0 | 0.24 | 0459 | 0.24 | 0.6 | 1.0 |
| 14 Prototype | | | 3.5 | 3.5 | 0.48 | 1.8 | 2.0 | 4.0 | 2.2 |

These data indicate that the compounds of the invention have a pronounced virucidal activity against simple- and multi-structured RNA- and DNA-containing viruses.

Example 17

In this experiment, the toxicity of the Formula I preparations were analyzed using the Ex Vivo Red Blood cell hemolysis assay (Human red blood cells). Human red blood cells were dissolved in PBS. Each compound was tested in 5 dilutions. Data are shown in table 6.

TABLE 6

Toxicity on MDCK Cells.

| Example No. | Acid | Weight range limits, Da | Concentration (mg/L) required to lyse 50% of the erythrocytes |
|---|---|---|---|
| 1 | HCl | up to 3000 | ≥500 |
| 2 | HCl | up to 10 000 | ≥250 |
| 3 | HCl | 1000-3000 | ≥500 |
| 4 | HCl | 2000-3000 | ≥500 |
| 5 | HCl | 3000-5000 | ≥250 |
| 6 to 05 | HCl | up to 3000 | ≥250 |
| 7 | HCl | up to 10 000 | ≥250 |
| 8 | $H_2SO_4$ | up to 10 00 | ≥250 |
| 9 | AcOH | up to 3000 | ≥500 |
| 10 | HCl | up to 2000 | ≥500 |
| 11 | HCl | up to 5000 | ≥250 |
| 12 | HCl | 5000-10 000 | ≥500 |
| 13 | HCl | 2000-10 000 | ≥250 |
| Prototype | | | 100 |

The biological activity and toxicity data in Examples 13-16 demonstrate the unexpected advantages of the Formula I preparations. Without being bound by any theory of the invention, it is believed that the inventive process affords polymer preparations having narrow and advantageous molecular weight distributions which provide high level activity against specific pathogens. Removal of certain low and high molecular weight components from the preparations produces Formula I fractions that have low toxicity, enhanced antimicrobial activity, facilitated penetration across biological membranes, advantageous disintegration profiles and other advantageous features. Certain fractions of the Formula I compounds have unique activity profiles which target specific microorganisms. For example, the Example 1 preparation shows high activity against multi-cellular fungi of the *Aspergillus* genus. The preparation in Example 4 is highly effective with respect to single-celled fungi of the *Candida* genus. The Example 11 preparation shows high activity against Gram-positive bacteria. The Example 2 preparation is active against Gram-negative bacteria. Mycobacteria are highly sensitive to the preparation in Example 12. The compounds in Examples 1, 2, 3, 10, and 13 each exhibit high activity against specific viruses. Thus, the prepared samples have unique and unexpected activity profiles useful for targeting specific types of pathogens.

Example 18

In this Example, the antitumor activity of the Formula I compounds was tested using the model of continuous Ehrlich solid tumor. The Formula I preparation was administered simultaneously with the tumor transplantation (0.2 ml of 0.01% solution) intraperitoneally. The control animals received water (which was used as the solvent for the drugs tested).

TABLE 7

Antitumor Action.

| Sample | Tumor size (mm³), days after transplantation | | | | | |
|---|---|---|---|---|---|---|
| | 7 days | 11 days | 14 days | 18 days | 22 days | 25 days |
| No. 1 | 92.6 | 191.8 | 276.9 | 357.3 | 579.4 | 613.4 |
| No. 3 | 83.4 | 177.0 | 253.9 | 312.5 | 542.6 | 631.9 |
| No. 8 | 71.5 | 149.8 | 244.1 | 423.6 | 602.7 | 688.5 |
| No. 10 | 101.7 | 211.2 | 307.5 | 508.6 | 599.5 | 730.4 |
| Control | 142.1 | 309.2 | 703.1 | 2095.0 | 3080.4 | 3360.5 |

The results indicate that the studied samples inhibit tumor growth in experimental animals.

Example 19

In this experiment, a model of continuous Ehrlich solid tumor was used to study combined effect of claimed product with anticancer drugs. The drugs were administered simultaneously with the tumor transplantation (0.2 ml of 0.01% solution) intraperitoneally. The control animals received water (used as solvent for the drugs tested).

TABLE 8

Antitumor Action.

| Sample | Tumor size (mm³), days after transplantation | | | | | |
|---|---|---|---|---|---|---|
| | 7 days | 11 days | 14 days | 18 days | 22 days | 25 days |
| No. 1 | 92.6 | 191.8 | 276.9 | 357.3 | 579.4 | 613.4 |
| Cisplatin | 72.4 | 180.7 | 243.3 | 345.8 | 548.2 | 607.7 |
| No. 1 + Cisplastin | 43.5 | 104.6 | 144.3 | 250.8 | 344.6 | 404.3 |
| Control | 142.1 | 309.2 | 703.1 | 2095.0 | 3080.4 | 3360.5 |

The results indicate that the studied sample together with anticancer drug inhibits tumor growth in experimental animals. As will be appreciated by a person of ordinary skill in the art, similar anticancer effect is expected to occur when Formula I preparations are combined with other anticancer drugs, e.g., alkylating agents, antimetabolites, purine antagonists, pyrimidine antagonists, plant alkaloids, antibiotics, hormonal agents, and miscellaneous anticancer drugs.

Example 20

Compounds herein were examined by MALDI-MS according to the method in Example 1. Table 9 lists mass values (m/z) of characteristic MH+ ions and their relative intensity in the mass spectrum of Examples 1, 1a, 1b, 1c, 1d, 6, 9, 10 in the range of m/z 480-2000 Da.

TABLE 9

Masses of MH+ ions and their relative intensity in the mass spectrum of the claimed product (Examples 1, 1a, 1b, 1c, 1d, 6, 9, 10) in the range of m/z 480-2000 Da.

| | | | | | |
|---|---|---|---|---|---|
| 483.3 (70) | 845.5 (12) | 1144.8 (8) | 1409.9 (11) | 1613.2 (51) | 1875.3 (24) |
| 498.3 (11) | 847.6 (24) | 1146.8 (4) | 1412.0 (31) | 1627.2 (11) | 1892.4 (27) |
| 523.3 (37) | 848.6 (16) | 1154.8 (10) | 1427.0 (8) | 1633.1 (11) | 1894.4 (9) |
| 540.4 (7) | 864.6 (41) | 1161.8 (8) | 1429.0 (18) | 1638.2 (8) | 1910.4 (17) |
| 563.3 (7) | 879.6 (8) | 1169.8 (14) | 1430.1 (23) | 1712.3 (19) | 1932.4 (19) |
| 565.3 (4) | 887.5 (7) | 1186.8 (19) | 1437.0 (10) | 1720.2 (18) | 1934.4 (9) |
| 582.4 (33) | 904.6 (18) | 1188.9 (92) | 1444.1 (7) | 1727.3 (8) | 1935.4 (7) |
| 608.4 (6) | 906.7 (100) | 1203.9 (18) | 1452.0 (19) | 1733.3 (7) | 1950.4 (9) |
| 622.4 (16) | 921.7 (15) | 1213.9 (9) | 1470.1 (17) | 1735.2 (8) | 1959.4 (11) |
| 624.4 (84) | 946.6 (60) | 1228.9 (58) | 1471.1 (60) | 1751.3 (8) | 1974.4 (10) |
| 639.4 (17) | 961.7 (7) | 1243.9 (12) | 1486.1 (18) | 1753.3 (13) | 1976.4 (6) |
| 664.4 (16) | 986.7 (16) | 1253.9 (10) | 1493.0 (14) | 1754.3 (23) | 1977.4 (11) |
| 665.4 (22) | 988.7 (27) | 1268.9 (18) | 1511.1 (42) | 1768.3 (36) | 1991.4 (11) |
| 679.4 (8) | 1003.7 (7) | 1270.9 (35) | 1526.1 (10) | 1774.2 (12) | 1993.5 (8) |
| 704.4 (3) | 1005.7 (39) | 1285.9 (4) | 1534.0 (9) | 1793.3 (10) | 1994.5 (19) |
| 706.4 (19) | 1020.8 (6) | 1288.0 (36) | 1551.1 (16) | 1794.3 (24) | |
| 723.5 (20) | 1028.7 (19) | 1295.9 (13) | 1553.1 (21) | 1808.3 (28) | |
| 746.5 (12) | 1030.7 (9) | 1303.0 (9) | 1568.1 (9) | 1816.2 (9) | |
| 748.5 (6) | 1045.7 (21) | 1310.9 (18) | 1570.2 (18) | 1818.3 (7) | |
| 763.5 (15) | 1047.8 (81) | 1328.0 (17) | 1579.1 (10) | 1833.3 (7) | |
| 765.6 (90) | 1062.8 (23) | 1330.0 (81) | 1585.2 (8) | 1835.3 (11) | |
| 780.6 (20) | 1087.8 (60) | 1345.0 (20) | 1591.1 (10) | 1836.3 (20) | |
| 805.5 (53) | 1102.8 (12) | 1370.0 (38) | 1593.1 (12) | 1850.3 (13) | |
| 806.5 (13) | 1127.8 (16) | 1371.0 (49) | 1610.2 (12) | 1852.4 (7) | |
| 820.5 (9) | 1129.8 (24) | 1385.0 (14) | 1612.2 (49) | 1868.4 (8) | |

TABLE 10

Masses of MH+ ions and their relative intensity in the mass spectrum of the claimed product (Examples 2, 7, 8, 11, 13) in the range of m/z 480-2000 Da.

| | | | | | |
|---|---|---|---|---|---|
| 483.3 (90) | 845.5 (8) | 1144.8 (8) | 1409.9 (11) | 1613.2 (15) | 1875.3 (14) |
| 498.3 (10) | 847.6 (11) | 1146.8 (4) | 1412.0 (31) | 1627.2 (11) | 1892.4 (5) |
| 523.3 (30) | 848.6 (15) | 1154.8 (10) | 1427.0 (8) | 1633.1 (11) | 1894.4 (3) |
| 540.4 (3) | 864.6 (41) | 1161.8 (8) | 1429.0 (18) | 1638.2 (8) | 1910.4 (3) |
| 563.3 (5) | 879.6 (6) | 1169.8 (14) | 1430.1 (23) | 1712.3 (4) | 1932.4 (4) |
| 565.3 (5) | 887.5 (8) | 1186.8 (19) | 1437.0 (10) | 1720.2 (10) | 1934.4 (2) |
| 582.4 (24) | 904.6 (18) | 1188.9 (70) | 1444.1 (7) | 1727.3 (8) | 1935.4 (3) |
| 608.4 (5) | 906.7 (50) | 1203.9 (13) | 1452.0 (19) | 1733.3 (2) | 1950.4 (7) |
| 622.4 (3) | 921.7 (15) | 1213.9 (8) | 1470.1 (17) | 1735.2 (3) | 1959.4 (6) |

TABLE 10-continued

Masses of MH+ ions and their relative intensity in the mass spectrum of the claimed product (Examples 2, 7, 8, 11, 13) in the range of m/z 480-2000 Da.

| | | | | | |
|---|---|---|---|---|---|
| 624.4 (90) | 946.6 (30) | 1228.9 (40) | 1471.1 (32) | 1751.3 (3) | 1974.4 (5) |
| 639.4 (15) | 961.7 (4) | 1243.9 (10) | 1486.1 (10) | 1753.3 (7) | 1976.4 (6) |
| 664.4 (20) | 986.7 (3) | 1253.9 (5) | 1493.0 (6) | 1754.3 (11) | 1977.4 (8) |
| 665.4 (20) | 988.7 (21) | 1268.9 (6) | 1511.1 (19) | 1768.3 (24) | 1991.4 (3) |
| 679.4 (4) | 1003.7 (3) | 1270.9 (15) | 1526.1 (4) | 1774.2 (12) | 1993.5 (2) |
| 704.4 (2) | 1005.7 (25) | 1285.9 (4) | 1534.0 (9) | 1793.3 (10) | 1994.5 (2) |
| 706.4 (6) | 1020.8 (6) | 1288.0 (13) | 1551.1 (16) | 1794.3 (24) | |
| 723.5 (23) | 1028.7 (19) | 1295.9 (5) | 1553.1 (21) | 1808.3 (19) | |
| 746.5 (3) | 1030.7 (9) | 1303.0 (3) | 1568.1 (9) | 1816.2 (6) | |
| 748.5 (5) | 1045.7 (21) | 1310.9 (3) | 1570.2 (5) | 1818.3 (5) | |
| 763.5 (10) | 1047.8 (70) | 1328.0 (10) | 1579.1 (6) | 1833.3 (3) | |
| 765.6 (100) | 1062.8 (20) | 1330.0 (53) | 1585.2 (8) | 1835.3 (3) | |
| 780.6 (25) | 1087.8 (29) | 1345.0 (20) | 1591.1 (4) | 1836.3 (6) | |
| 805.5 (03) | 1102.8 (10) | 1370.0 (38) | 1593.1 (10) | 1850.3 (4) | |
| 806.5 (10) | 1127.8 (18) | 1371.0 (49) | 1610.2 (6) | 1852.4 (4) | |
| 820.5 (15) | 1129.8 (22) | 1385.0 (14) | 1612.2 (34) | 1868.4 (5) | |

TABLE 11

Masses of MH+ ions and their relative intensity in the mass spectrum of the claimed product (Examples 3, 4, 5, 13) in the range of m/z 480-2000 Da.

| | | | | | |
|---|---|---|---|---|---|
| 483.3 (10) | 845.5 (12) | 1144.8 (8) | 1409.9 (11) | 1613.2 (33) | 1875.3 (24) |
| 498.3 (1) | 847.6 (24) | 1146.8 (4) | 1412.0 (31) | 1627.2 (11) | 1892.4 (27) |
| 523.3 (3) | 848.6 (16) | 1154.8 (10) | 1427.0 (8) | 1633.1 (11) | 1894.4 (9) |
| 540.4 (3) | 864.6 (80) | 1161.8 (8) | 1429.0 (18) | 1638.2 (8) | 1910.4 (17) |
| 563.3 (1) | 879.6 (15) | 1169.8 (11) | 1430.1 (23) | 1712.3 (29) | 1932.4 (22) |
| 565.3 (1) | 887.5 (7) | 1186.8 (10) | 1437.0 (10) | 1720.2 (20) | 1934.4 (9) |
| 582.4 (17) | 904.6 (18) | 1188.9 (98) | 1444.1 (7) | 1727.3 (8) | 1935.4 (7) |
| 608.4 (9) | 906.7 (88) | 1203.9 (18) | 1452.0 (19) | 1733.3 (7) | 1950.4 (9) |
| 622.4 (10) | 921.7 (21) | 1213.9 (9) | 1470.1 (17) | 1735.2 (8) | 1959.4 (11) |
| 624.4 (65) | 946.6 (25) | 1228.9 (58) | 1471.1 (60) | 1751.3 (8) | 1974.4 (10) |
| 639.4 (12) | 961.7 (710) | 1243.9 (12) | 1486.1 (18) | 1753.3 (13) | 1976.4 (67) |
| 664.4 (1) | 986.7 (5) | 1253.9 (10) | 1493.0 (14) | 1754.3 (23) | 1977.4 (10) |
| 665.4 (2) | 988.7 (2) | 1268.9 (18) | 1511.1 (25) | 1768.3 (36) | 1991.4 (6) |
| 679.4 (5) | 1003.7 (7) | 1270.9 (10) | 1526.1 (10) | 1774.2 (12) | 1993.5 (10) |
| 704.4 (3) | 1005.7 (95) | 1285.9 (4) | 1534.0 (9) | 1793.3 (10) | 1994.5 (19) |
| 706.4 (1) | 1020.8 (6) | 1288.0 (95) | 1551.1 (16) | 1794.3 (24) | |
| 723.5 (2) | 1028.7 (20) | 1295.9 (13) | 1553.1 (21) | 1808.3 (28) | |
| 746.5 (2) | 1030.7 (9) | 1303.0 (9) | 1568.1 (9) | 1816.2 (9) | |
| 748.5 (3) | 1045.7 (21) | 1310.9 (18) | 1570.2 (51) | 1818.3 (7) | |
| 763.5 (5) | 1047.8 (100) | 1328.0 (17) | 1579.1 (10) | 1833.3 (7) | |
| 765.6 (70) | 1062.8 (8) | 1330.0 (81) | 1585.2 (8) | 1835.3 (11) | |
| 780.6 (2) | 1087.8 (23) | 1345.0 (10) | 1591.1 (10) | 1836.3 (20) | |
| 805.5 (16) | 1102.8 (12) | 1370.0 (10) | 1593.1 (12) | 1850.3 (13) | |
| 806.5 (1) | 1127.8 (16) | 1371.0 (24) | 1610.2 (12) | 1852.4 (7) | |
| 820.5 (1) | 1129.8 (24) | 1385.0 (14) | 1612.2 (35) | 1868.4 (8) | |

Example 21

In this example the efficacy of the Example 1 preparation was tested against pulmonary bacterial pathogens in cystic fibrosis patients. The results of this study are shown in Table 12.

TABLE 12

Activity of Example1 Against Resistant Strains Found in CF Patients.

| Pathogen | Number of strains | No. 1 (MIC) | No. 11 (MIC) | TOBI (MIC) | Cayston (MIC) |
|---|---|---|---|---|---|
| P. aeruginosa | 15 | 0.25-1.0 | 0.5 | 0.5-1.0 | 2.0-8.0 |
| MDR-PA | 10 | 0.5-8.0 | 0.5-4.0 | 128-256 | 128-256 |
| S. aureus MSSA | 10 | 0.25-0.5 | 0.25-0.5 | 0.5-2.0 | 8.0-64.0 |
| S. aureus MRSA | 10 | 0.25-4.0 | 0.25-2.0 | 64-256 | 64-128 |
| H. Influenzae | 10 | 0.25-1.0 | 0.5-10 | 0.5-2.0 | 0.25-4.0 |
| S. maltophilia | 10 | 0.05-0.5 | 0.05-0.25 | 1.0-2.0 | 8.0-32.0 |
| A. fumigatus | 5 | 0.25-0.5 | 0.5-1.0 | ineffective | ineffective |
| C. albicans | 5 | 0.25-0.5 | 0.25-0.5 | ineffective | ineffective |

These data show that the polymer fractions of the invention exhibit wide spectrum activity against resistant strains commonly found in CF patients. The inventive polymer fractions have enhanced activity over conventional drugs such as TOBI and Cayston.

Example 22

In this example the efficacy of the preparations were tested against an animal model of mixed respiratory infection.

Methods:

The potency of Example Nos. 1, 5 and 10 were examined against bacterial isolates from patients with cystic fibrosis. The MICs values were determined by the broth macrodilution method according to the CLSI guideline. For the in vivo studies, 8-week-old C57BL/6 mice were intranasally infected with *P. aeruginosa* MR-6 ($2 \times 10^7$ cfu/mouse)+*A. fumigatus* ($6 \times 10^6$ cfu/mouse). Treatment was initiated 12 h after infection with Example Nos. 1, 5, and 10, or with tobramycin or aztreonam, administered by intranasal inhalation at 32×MIC.

Results:

Example Nos. 1, 5 and 10 exhibited a high level of antimicrobial activity with the MIC 0.25-0.5 mg/L against *A. fumigatus* and 1.0-4.0 mg/L against *P. aeruginosa*. Tobramycin and aztreonam were less active; tobramycin yielded an MIC of 16-32 mg/L for *P. aerugnosa* and was not active against *A. fumigatus*; aztreonam yielded an MIC of 64 mg/L for *P. aeruginosa* and was not active against *A. fumigatus*.

TABLE 13

Percent mortality 96 h post infection.

| Compound | P. aeruginosa | A. fumigatus | P. aeruginosa + A. fumigatus |
|---|---|---|---|
| Untreated control | 40% | 60% | 100% |
| No1 | 0% | 0% | 10% |
| No5 | 0% | 0% | 10% |
| No11 | 10% | 0% | 10% |
| Tobramycin | 20% | 40% | 50% |
| Aztreonam | 20% | 30% | 60% |

Example 23

In this example the efficacy of the preparations (Example Nos. 1 and 10) were tested for treatment of human sinusitis. Patients (15 total) with sinusitis undergo direct sinus puncture and instillation of 2 m of 0.05% No. 1 (5 patients) and 0.05% No. 10 (5 patients). Control patients were instilled with sterile 0.9% saline (5 patients). Clinical efficacy was considered as normalization of temperature and decrease of the pain. Microbiological efficacy was determined as the decrease of the number of CFU after the plating to the Columbia agar for 24 h at 37° C. after 48 h post instillation.

TABLE 14

Efficacy of compounds for the treatment of sinusitis

| | Number of CFU | | |
|---|---|---|---|
| Compound | Before treatment | 48 hours after treatment | Clinical recovery |
| Control | 9 | 9 | 6th day |
| No. 1 | 10 | 3 | $2^{nd}$ day |
| No. 10 | 12 | 1 | $2^{nd}$ day |

Example 24

In this example the efficacy of the preparations (Example Nos. 1 and 4) were tested for treatment of human cystitis. Patients (15 total) with cystitis underwent bladder instillation with 10 ml of 0.005% Example No. 1 (5 patients) and 0.1% No. 4 (5 patients). Control patients were instilled with sterile 0.9% saline (5 patients). Microbiological efficacy was determined as a decrease in the number of CFU after the plating to the Columbia agar for 24 h at 37° C. after the 48 h post instillation.

TABLE 15

Efficacy of compounds for the treatment of sinusitis

| | Number of CFU | |
|---|---|---|
| Compound | Before treatment | 48 hours after treatment |
| Control | 12 | 9 |
| No1 | 14 | 3 |
| No 4 | 16 | 1 |

Example 25

In this example the efficacy of the preparations were tested against bacteriophages. In particular, the potency of Example Nos. 1, 3, 9, 10, 12 and 13 all at 0.05% against bacteriophages that infect *Salmonella* spp was examined. The phages were enumerated by Gratia's method (Kropinski et al. "Enumeration of bacteriophages by double agar overlay plaque assay." Bacteriophages: Methods and Protocols, Volume 1: Isolation, Characterization, and Interactions, Humana Press, 2009, vol. 501, 69-76). Bacteriophages were incubated with compounds for 5 minutes, then filtered and washed with PBS buffer. The bacteriophage sampler were then used in a plaque assay-based method to study their activity.

TABLE 16

Efficacy of compounds against bacteriophages

| Compound | Bacteriophage' titer |
|---|---|
| Control (PBS) | $7.5 \times 10^5$ |
| No. 1 | 0 |
| No. 3 | 0 |
| No. 9 | 0 |
| No. 10 | 0 |
| No. 12 | 0 |
| No. 13 | 0 |

Example 26

In this example, the efficacy of Examples 1, 10 and 13 were tested against multi-drug resistant microorganisms.

Bacterial strains tested: *Pseudomonas aeruginosa* AGR 18 and MR23 multiresistant. Fungal strain: *Candida glabrata* CG15, VT18 resistant to Amphotericin B and Voriconazole Microbiological efficacy was determined as the Minimal Inhibitory Concentration. The MIC was defined as the lowest concentration of antibiotic that completely inhibited visible growth The bactericidal activities of Examples 1, 10 and 13 against multiresistant *P. aeruginosa* isolates are shown below in Table 17.

TABLE 17

Efficacy of compounds against *P. aeruginosa*

| Antibacterials | Susceptibility breakpoint (µg/ml) | *P. aeruginosa* strain MIC (µg/ml) | |
|---|---|---|---|
| | | AGR 18 | MR23 |
| Ex. 1 | ND | 2 | 4 |
| Ex. 10 | ND | 1 | 2 |
| Ex. 13 | ND | 2 | 2 |
| Amikacin | ≤16 | 128 | 256 |
| Aztreonam | ≤8 | 32 | 128 |
| Ceftazidime | ≤8 | 32 | 32 |
| Piperacillin | ≤16 | >256 | 256 |
| Tobramycin | ≤4 | 32 | 32 |

The bactericidal activities of Examples 1, 10 and 13 against multiresistant *C. glabrata* isolates are shown below in Table 18.

TABLE 18

Efficacy of compounds against *P. aeruginosa*

| Anti-fungals | Susceptibility breakpoint (µg/ml) | | | Minimal fungicidal concentration (µg/ml) against yeasts | |
|---|---|---|---|---|---|
| | S | I | R | *C. glabrata* CG1514053 | *C. albicans* VT18 |
| No1 | | ND$^a$ | | 0.06 | 0.03 |
| No10 | | ND$^a$ | | 0.06 | 0.12 |
| No13 | | ND$^a$ | | 0.12 | 0.06 |
| AMB | | ND$^a$ | | 4 | 8 |
| VRZ | ≤0.12 | 0.25-0.5 | ≥1 | 8 | 4 |

$^a$CLSI and EUCAST have not set susceptibility breakpoints for AMB and Ex 1, 10, 13. I—intermediate; R—resistant; S—susceptible.

Example 27

In this example, the efficacy of the inventive preparations was tested against Vancomycin resistant *S. aureus* (VRSA)

The MICs were determined using a broth macrodilution method with cation-adjusted Mueller-Hinton broth II (Becton Dickinson) at standard inoculum ($10^5$ cfu/mL) following the CLSI recommendations. The cultures used in this study were bacterial clinical isolates from human infections. The data for these experiments is shown in Table 19.

TABLE 19

Minimum inhibitory concentrations of preparations against *S. aureus* isolates.

| Antibiotic | Susceptibility breakpoint (µg/ml) | VRSA strain MIC (µg/ml) | | | MSSA strain MIC (µg/ml) ATCC 29213 |
|---|---|---|---|---|---|
| | | VT-V-18 | VT-V-25 | VT-A-199 | |
| Ex. 1 | ND | 0.06 | 0.125 | 0.06 | 0.125 |
| Ex. 5 | ND | 0.125 | 0.25 | 0.25 | 0.5 |
| Ex. 9 | ND | 0.06 | 0.25 | 0.06 | 0.5 |
| Ciprofloxacin | <4.0 | 64 | 16 | 256 | 0.5 |
| Ampicillin | <0.5 | 64 | 32 | 16 | 0.25 |
| Vancomycin | <16.0 | 16 | 1 | 16 | 0.5 |
| Meropenem | <4.0 | 32 | 128 | 128 | 0.125 |
| Clindamycin | <4.0 | 4 | 2 | 2 | 0.125 |
| Daptomycin | <1.0 | 0.125 | 0.25 | 0.5 | 0.25 |

Example 28

In this example, the efficacy of the inventive preparations was tested against preformed biofilms. Specifically, the efficacy of Example 1 against preformed 24 h old biofilms was tested. The MICs for antimicrobials were determined by the broth macrodilution method according to CLSI guidelines. A standard bacterial inoculum of $5 \times 10^5$ colony forming units (CFU)/mL was used. Serial 2-fold dilutions of the antimicrobials were prepared in cation-adjusted MHB. The MIC was defined as the lowest concentration of antibiotic that completely inhibited visible growth.

In each well of a 96-well flat-bottom polystyrene tissue culture microtiter plate (Sarstedt, Numbrecht, Germany), 200 µL of a standardized *P. aeruginosa* inoculum ($5 \times 10^5$ CFU/mL) in cation-adjusted MHB were added. Following a 24 h incubation at 37° C., biofilm samples were washed twice with phosphate-buffered saline to remove non-adherent bacteria and then exposed for 24 h to 200 µL of MHB containing the inventive preparations at 1, 2, 4, 8, 16, 32, and 64× the MIC. Untreated biofilms were used as the negative controls. After the exposure, well contents were aspirated to prevent antimicrobial carryover and each well was washed three times with sterile deionized water.

To estimate the CFU number, biofilms were scraped thoroughly, with particular attention to the well edges (11). The well contents were aspirated, placed in 1 mL of isotonic phosphate buffer (0.15 M, pH 7.2), and the total CFU number was determined by serial dilution and plating on Mueller-Hinton agar. Data were converted to a log 10 scale and compared to untreated controls.

The MBECs were determined as the concentrations of drug that killed 50 ($MBEC_{50}$), 90 ($MBEC_{90}$), and 100% ($MBEC_{100}$) of the bacteria in preformed biofilms. MBEC sensitivities were determined using the 2012 Clinical and Laboratory Standards Institute guidelines for interpretation. All assays included a minimum of 3 replicates and were repeated in 3 independent experiments. The results of these experiments is shown in Table 20.

TABLE 20

Susceptibility results for Example 1 preparations agaisnt *P. aeruginosa*.

| Isolate | $MBEC_{50}$ (µg/ml) | $MBEC_{90}$ (µg/ml) | $MBEC_{100}$ (µg/ml) |
|---|---|---|---|
| *P. aeruginosa* AGR14 | 8 | 32 | 256 |
| *P. aeruginosa* VT-CF-234 | 2 | 4 | 32 |

Example 29

In this example, the efficacy of the preparations was tested General treatment of surfaces. We studied the ability of Example 7 to sterilize water in a pond, having dimensions of 7 feet×5 feet×2 feet (width×length×height). Prior to the examination the water was taken from the pond and filtered and plated to onto Mueller-Hinton agar plates (Oxoid Ltd., London, England) and incubated at 37° C. overnight. The estimate colony forming units number was around 41 log 10 CFU/ml. After the adding to the water testing compound Example 7 to the final concentration 0.01%, and plating to the Mueller-Hinton agar plates (Oxoid Ltd., London, England) and incubated at 37° C. overnight there was no visible bacterial growth.

Example 30

In this example, the fractionated preparation described in Example 3 was tested in a cancer cell screen.

Methods:

Human cell lines of a cancer screening panel were grown in RPMI 1640 medium containing 5% fetal bovine serum and 2 mM L-glutamine. Cells were inoculated in 96 well microtiter plates in 100 µL. of medium at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of the Example 3.

After 24 h, two plates of each cell line were fixed in situ with TCA, to represent a control measurement of the cell population for each cell line at the time of addition of Example 3 (Tz). Example 3 was solubilized in dimethyl sulfoxide at 400-fold the desired final maximum test concentration and stored frozen prior to use. At the time of addition, an aliquot of frozen concentrate of Example 3 was thawed and diluted to twice the desired final maximum test concentration with complete medium containing 50 µg/ml gentamicin. Additional four, 10-fold or ½ log serial dilutions are made to provide a total of five concentrations of Example 3 plus control. Aliquots of 100 µl of the different dilutions were added to the appropriate microtiter wells containing 100 µl of medium, resulting in the required final concentrations of Example 3 in each sample.

Following addition of Example 3, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 µl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µl of 80% TCA (final concentration, 16% TCA). Using the seven absorbance measurements [time zero, (Tz), control growth, (C), and test growth in the presence of Example 3 at the five concentration levels (Ti)], the percentage growth was calculated for each Example 3 concentrations level. Percentage growth inhibition was calculated as follows:

$$[(Ti-Tz)/(C-Tz)] \times 100 \text{ for concentrations for which } Ti >/= Tz$$

$$[(Ti-Tz)/Tz] \times 100 \text{ for concentrations for which } Ti < Tz$$

Three dose response parameters were calculated. Growth inhibition of 50% (GI50) was calculated from [(Ti-Tz)(C-Tz)]×100=50, which is the Example 3 concentration resulting in a 50% reduction in the net protein increase (as measured by SRB staining) in control cells during the drug incubation. The concentration of Example 3 resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment is calculated from [(Ti-Tz)/Tz]×100=−50. Values are calculated for each of these three parameters if the level of activity is reached; however, if the effect is not reached or is exceeded, the value for that parameter is expressed as greater or less than the maximum or minimum concentration tested.

The list of human cancer cell lines used in the in vitro screen is shown in Table 21. The cell lines are maintained at NCI-Frederick.

TABLE 21

Cell Lines Tested in In Vitro Screen

| Cell Line Name | Panel Name | Doubling Time | Inoculation Density |
|---|---|---|---|
| CCRF-CEM | Leukemia | 26.7 | 40000 |
| HL-60(TB) | Leukemia | 28.6 | 40000 |
| K-562 | Leukemia | 19.6 | 5000 |
| MOLT-4 | Leukemia | 27.9 | 30000 |
| RPMI-8226 | Leukemia | 33.5 | 20000 |
| SR | Leukemia | 28.7 | 20000 |
| A549/ATCC | Non-Small Cell Lung | 22.9 | 7500 |
| EKVX | Non-Small Cell Lung | 43.6 | 20000 |
| HOP-62 | Non-Small Cell Lung | 39 | 10000 |
| HOP-92 | Non-Small Cell Lung | 79.5 | 20000 |
| NCI-H226 | Non-Small Cell Lung | 61 | 20000 |
| NCI-H23 | Non-Small Cell Lung | 33.4 | 20000 |
| NCI-H322M | Non-Small Cell Lung | 35.3 | 20000 |
| NCI-H460 | Non-Small Cell Lung | 17.8 | 7500 |
| NCI-H522 | Non-Small Cell Lung | 38.2 | 20000 |
| COLO 205 | Colon | 23.8 | 15000 |
| HCC-2998 | Colon | 31.5 | 15000 |
| HCT-116 | Colon | 17.4 | 5000 |
| HCT-15 | Colon | 20.6 | 10000 |
| HT29 | Colon | 19.5 | 5000 |
| KM12 | Colon | 23.7 | 15000 |
| SW-620 | Colon | 20.4 | 10000 |
| SF-268 | CNS | 33.1 | 15000 |
| SF-295 | CNS | 29.5 | 10000 |
| SF-539 | CNS | 35.4 | 15000 |
| SNB-19* | CNS | 34.6 | 15000 |
| SNB-75 | CNS | 62.8 | 20000 |
| U251* | CNS | 23.8 | 7500 |
| LOX IMVI | Melanoma | 20.5 | 7500 |
| MALME-3M | Melanoma | 46.2 | 20000 |
| M14 | Melanoma | 26.3 | 15000 |
| MDA-MB-435** | Melanoma | 25.8 | 15000 |
| SK-MEL-2 | Melanoma | 45.5 | 20000 |
| SK-MEL-28 | Melanoma | 35.1 | 10000 |
| SK-MEL-5 | Melanoma | 25.2 | 10000 |
| UACC-257 | Melanoma | 38.5 | 20000 |
| UACC-62 | Melanoma | 31.3 | 10000 |
| IGR-OV1 | Ovarian | 31 | 10000 |
| OVCAR-3 | Ovarian | 34.7 | 10000 |
| OVCAR-4 | Ovarian | 41.4 | 15000 |
| OVCAR-5 | Ovarian | 48.8 | 20000 |
| OVCAR-8 | Ovarian | 26.1 | 10000 |
| NCI/ADR-RES | Ovarian | 34 | 15000 |
| SK-OV-3 | Ovarian | 48.7 | 20000 |
| 786-0 | Renal | 22.4 | 10000 |
| A498 | Renal | 66.8 | 25000 |
| ACHN | Renal | 27.5 | 10000 |
| CAKI-1 | Renal | 39 | 10000 |
| RXF 393 | Renal | 62.9 | 15000 |
| SN12C | Renal | 29.5 | 15000 |
| TK-10 | Renal | 51.3 | 15000 |

TABLE 21-continued

Cell Lines Tested in In Vitro Screen

| Cell Line Name | Panel Name | Doubling Time | Inoculation Density |
|---|---|---|---|
| UO-31 | Renal | 41.7 | 15000 |
| PC-3 | Prostate | 27.1 | 7500 |
| DU-145 | Prostate | 32.3 | 10000 |
| MCF7 | Breast | 25.4 | 10000 |
| MDA-MB-231/ATCC | Breast | 41.9 | 20000 |
| MDA-MB-468 | Breast | 62 | 2000 |
| HS 578T | Breast | 53.8 | 20000 |
| MDA-N | Breast | 22.5 | 15000 |
| BT-549 | Breast | 53.9 | 20000 |
| T-47D | Breast | 45.5 | 20000 |

Not Available

*Single nucleotide polymorphism (SNP) array analysis has demonstrated that the SNB-19 and U251 lines are derived from the same individual. (Garraway L A, et al. Integrative genomic analyses identify MITF as a lineage survival oncogene amplified in malignant melanoma. Nature. 2005 Jul. 7; 436(7047): 117-22).

**MDA-MB-435, a member of the NCI-DTP panel of 60 human tumor cell lines, has been used for decades as a model of metastatic human breast cancer. This cell line was derived at M. D. Anderson in 1976 from a pleural effusion from a 31-year old woman with a history of breast cancer (Cailleau R, Olive M, Cruciger Q V. Long-term human breast carcinoma cell lines of metastatic origin: preliminary characterization. In Vitro. 1978 November; 14(11): 911-5.; Brinkley B R, Beall P T, Wible L J, Mace M L, Turner D S, Cailleau R M. Variations in cell form and cytoskeleton in human breast carcinoma cells in vitro. Cancer Res. 1980 September; 40(9): 3118-29.

Figure 2:
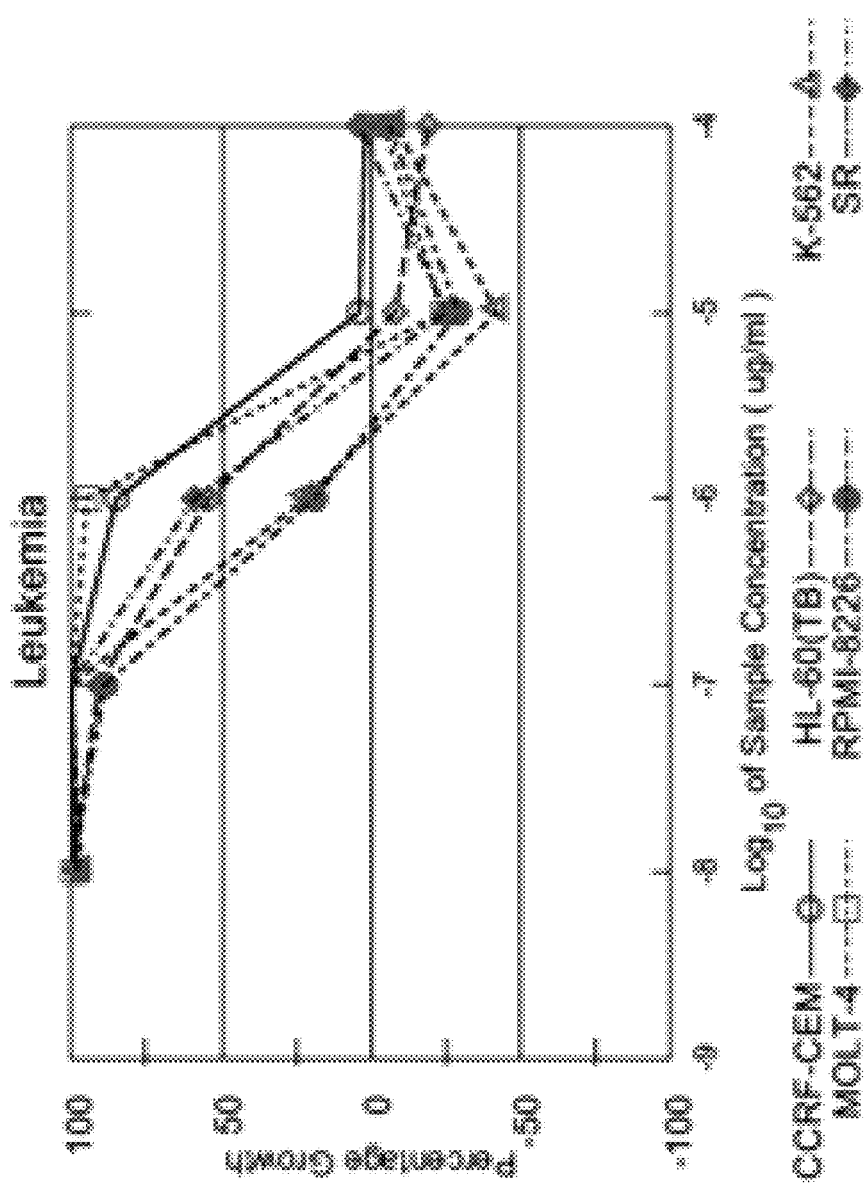
FIG. 2 shows dose response curves of cancer cells grown in the presence of the compound preparation of the invention as described in Example 30.
Figure 2:
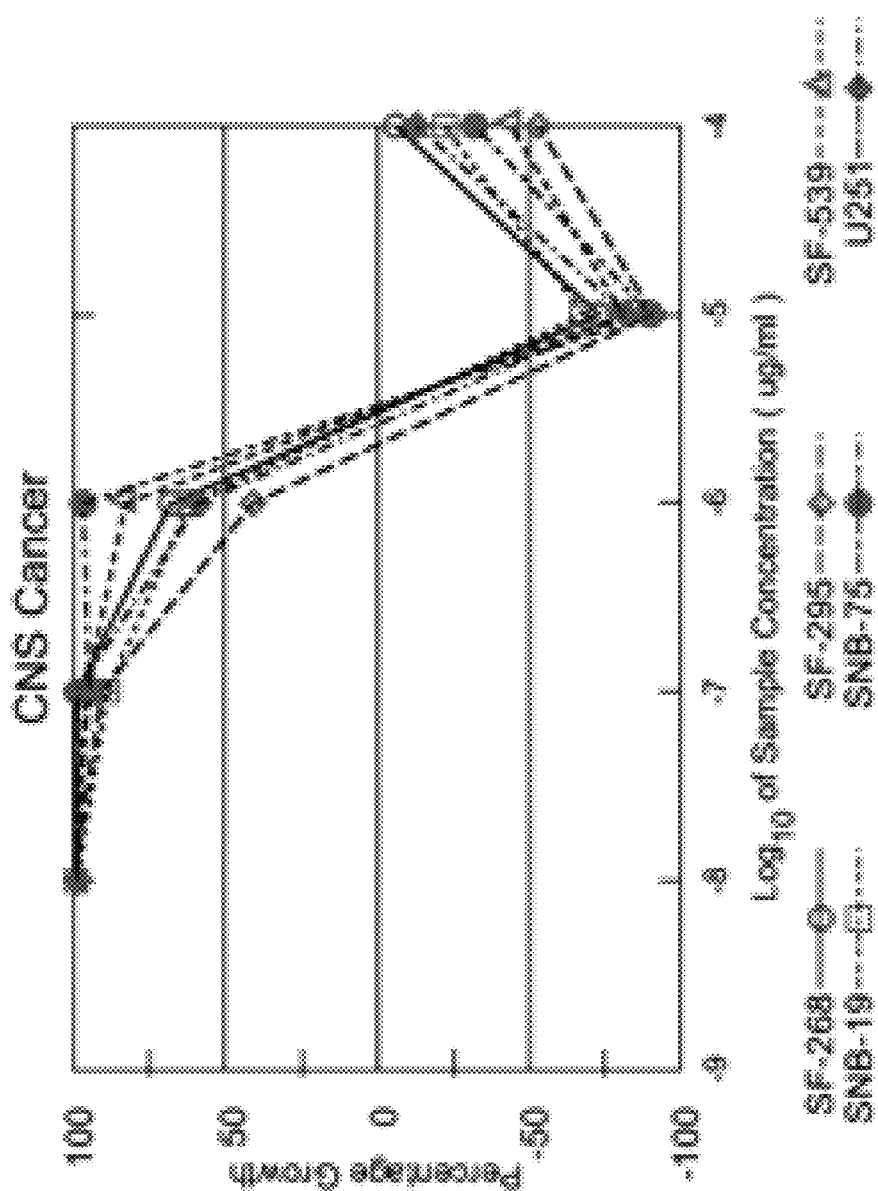
Figure 2:
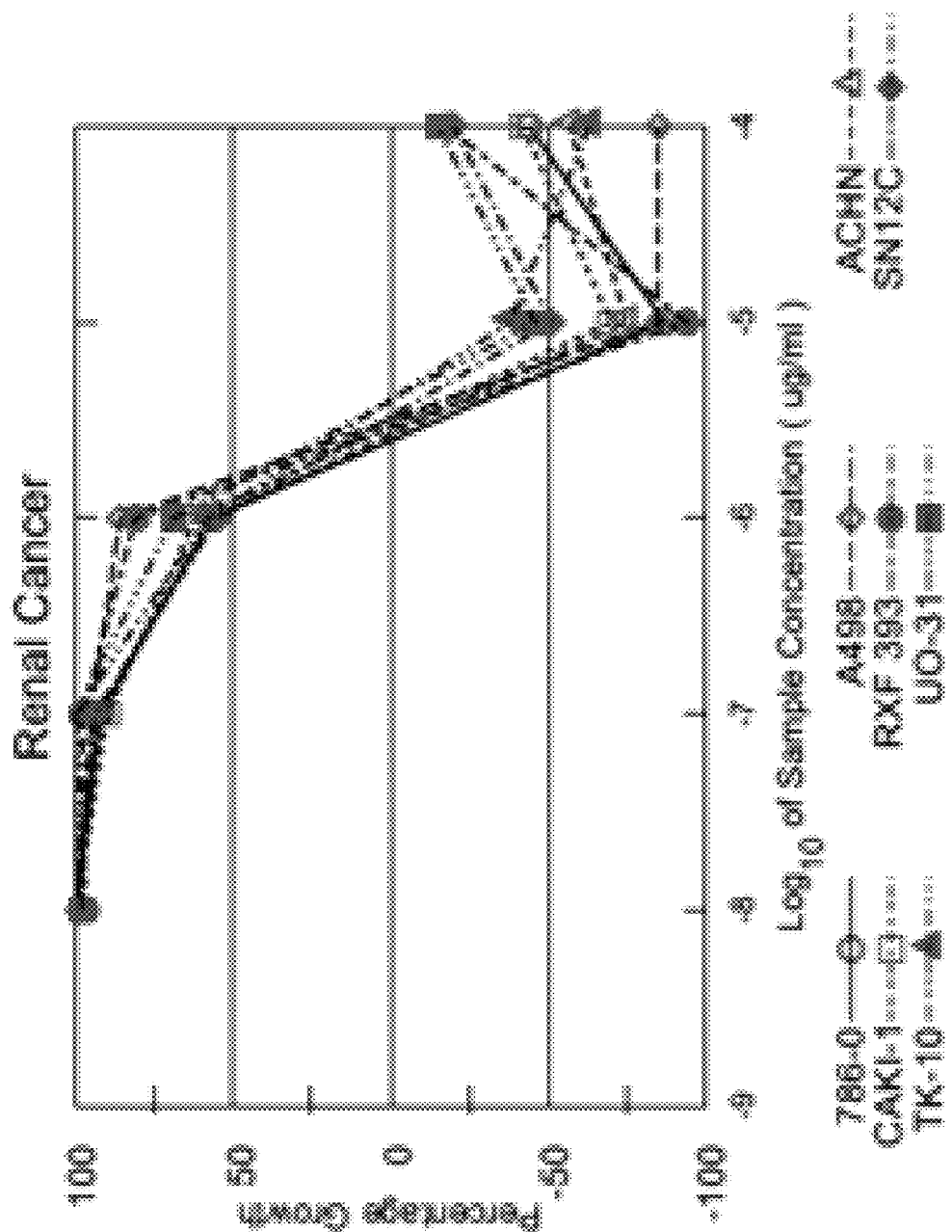
Figure 2:
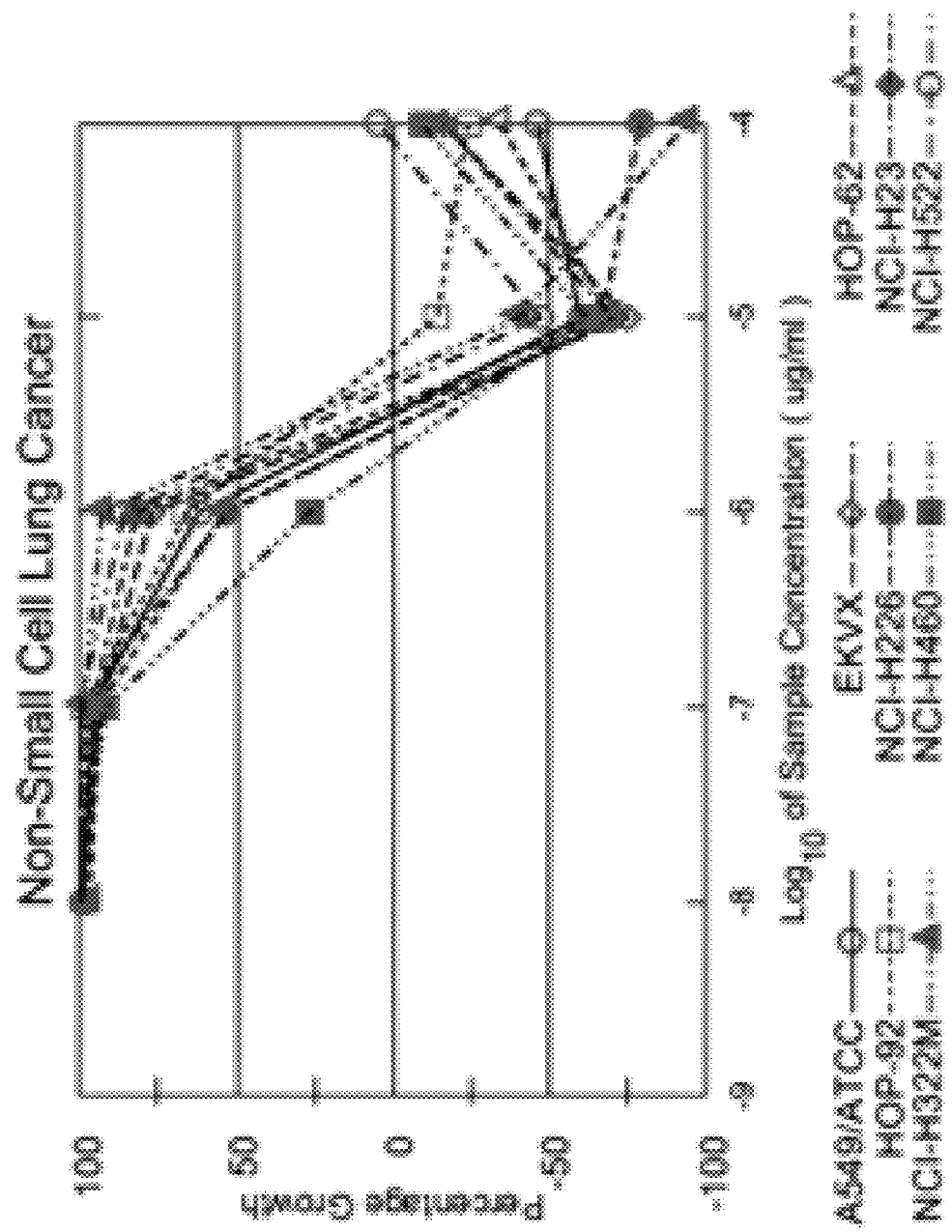
Figure 2:
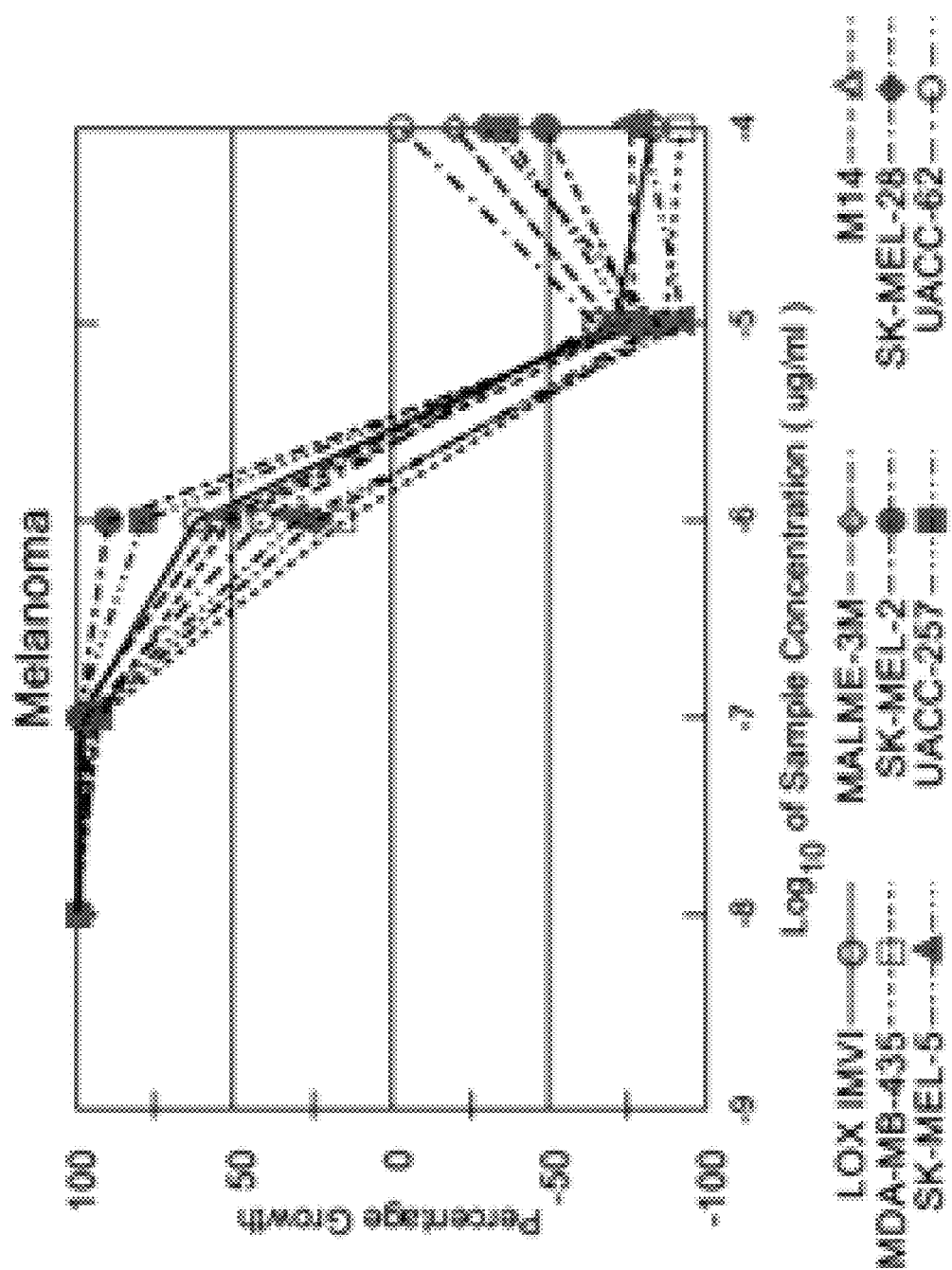
Figure 2:
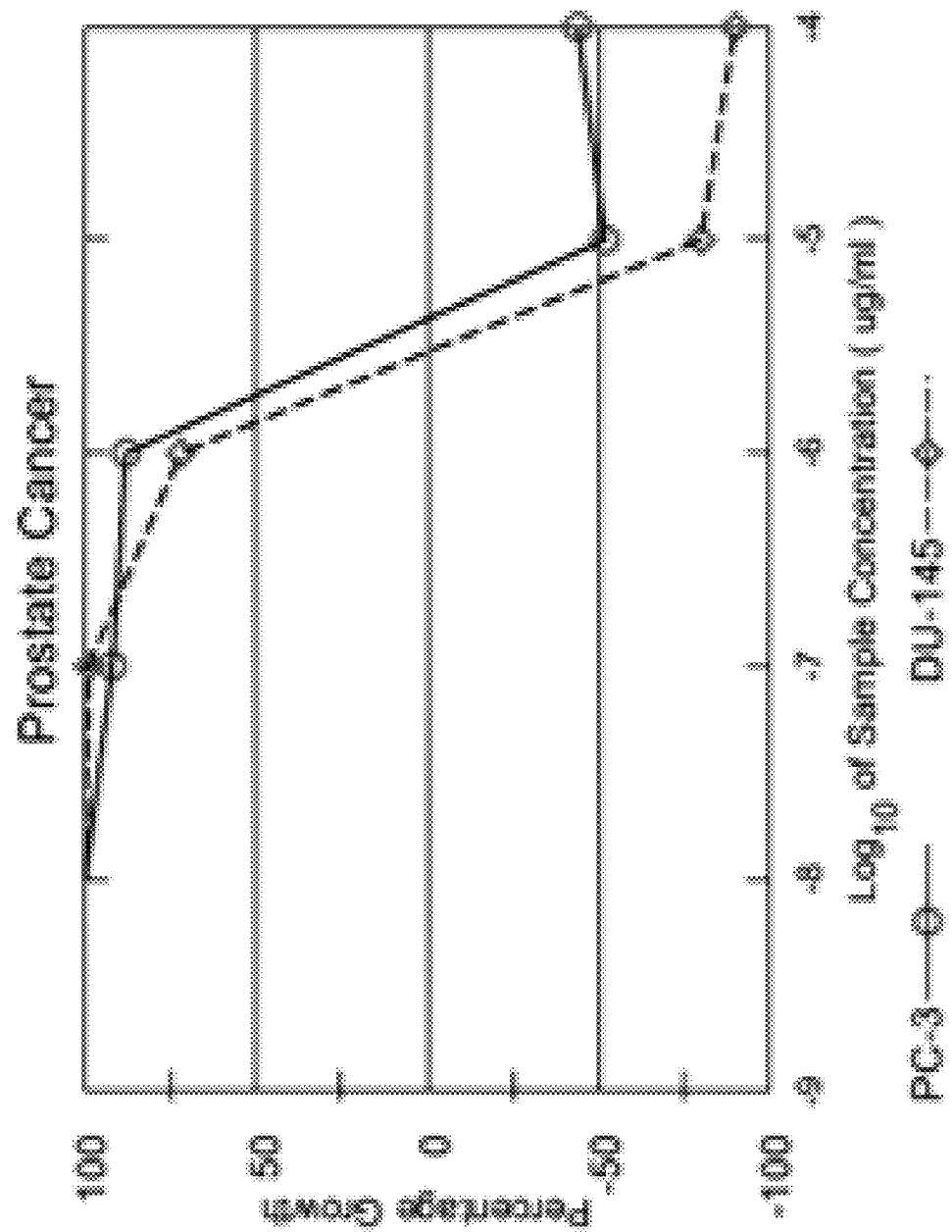
Figure 2:
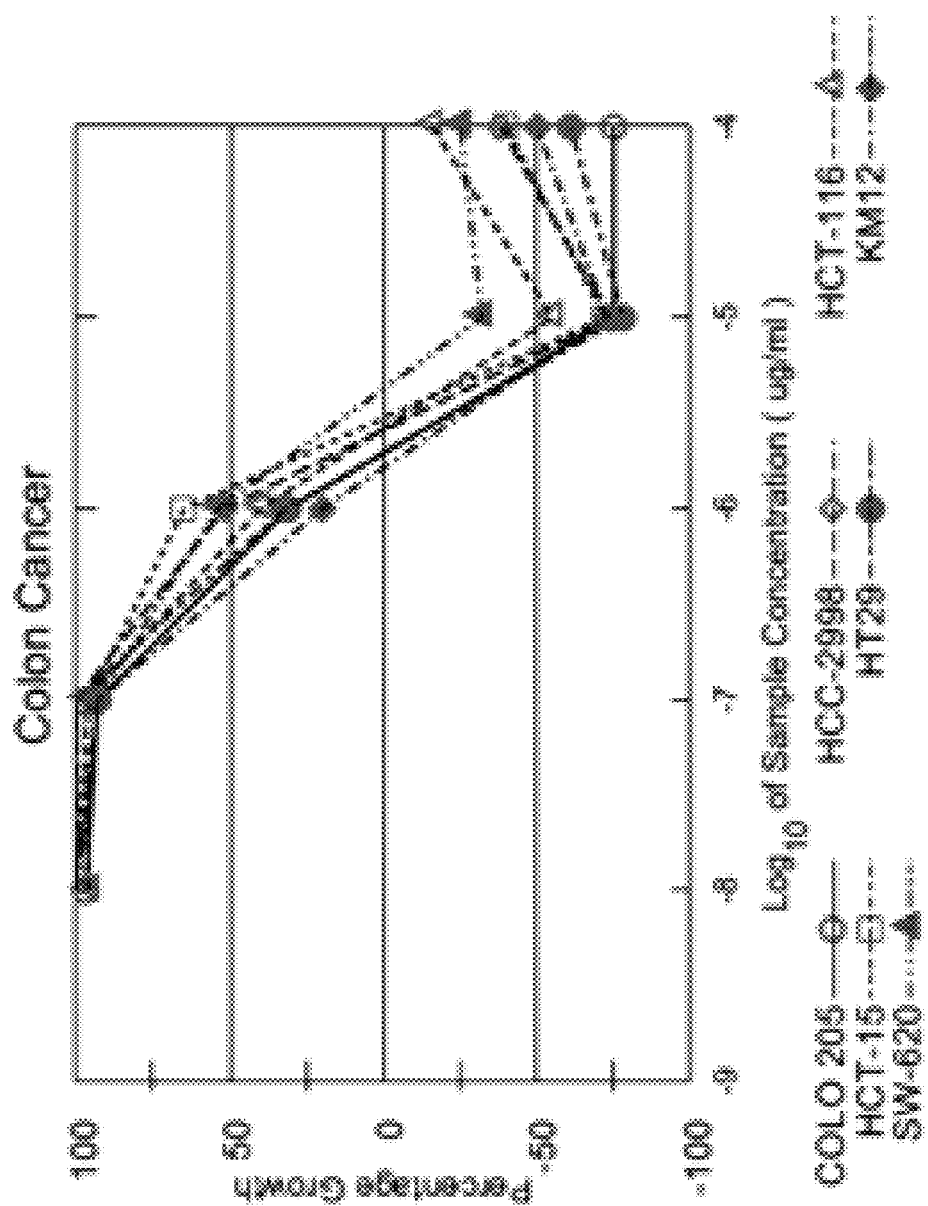
Figure 2:
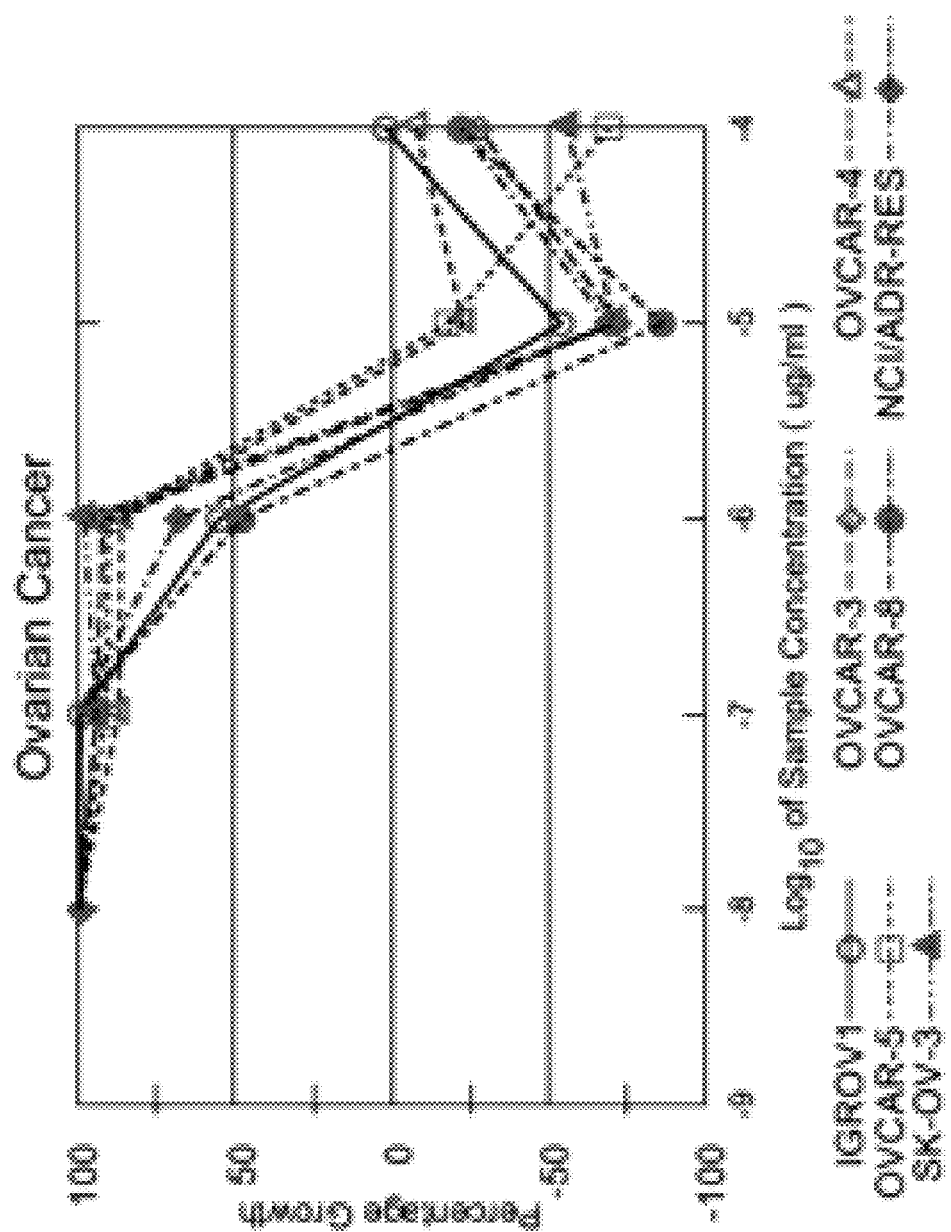
Figure 2:
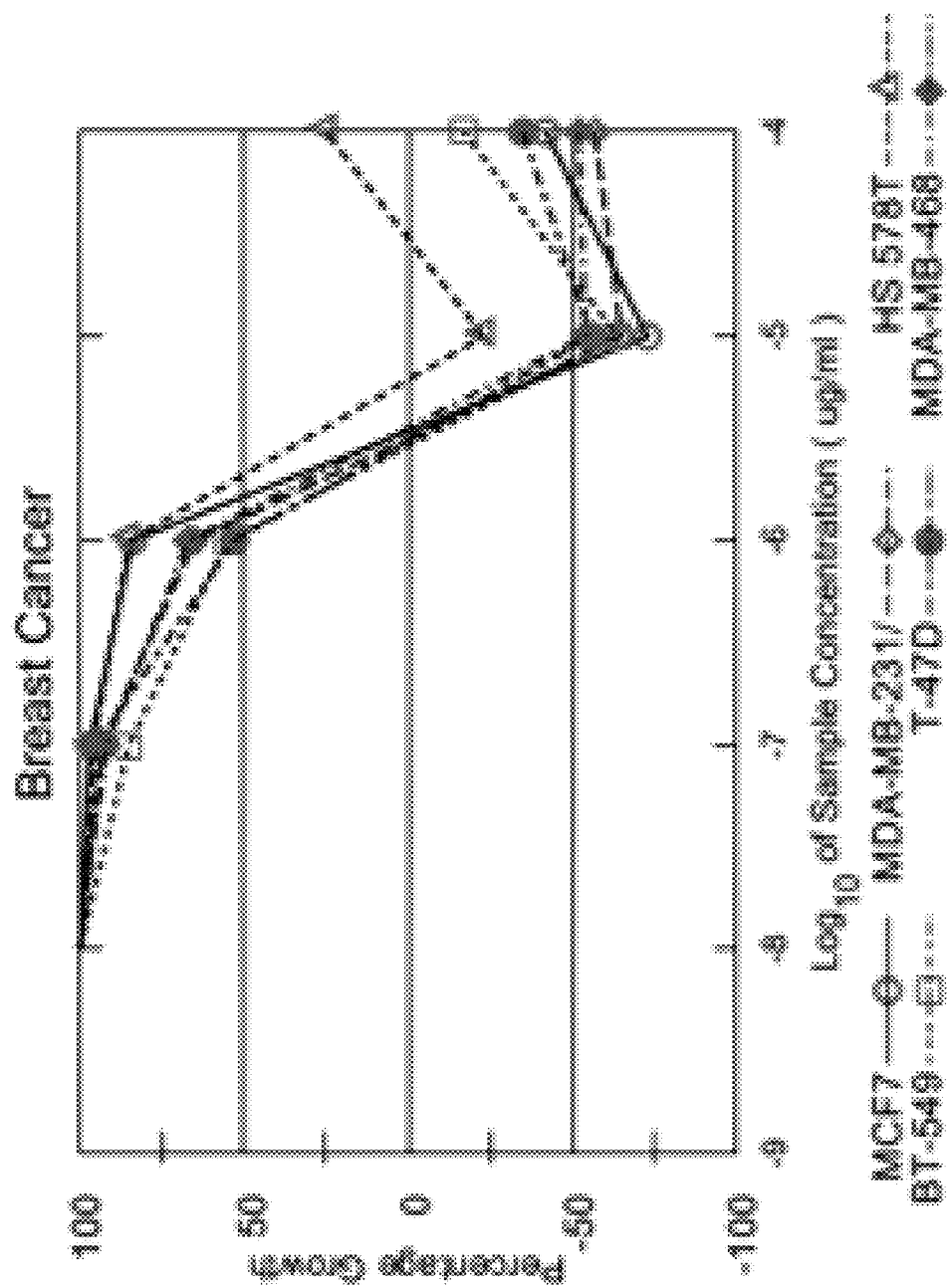
Figure 3:
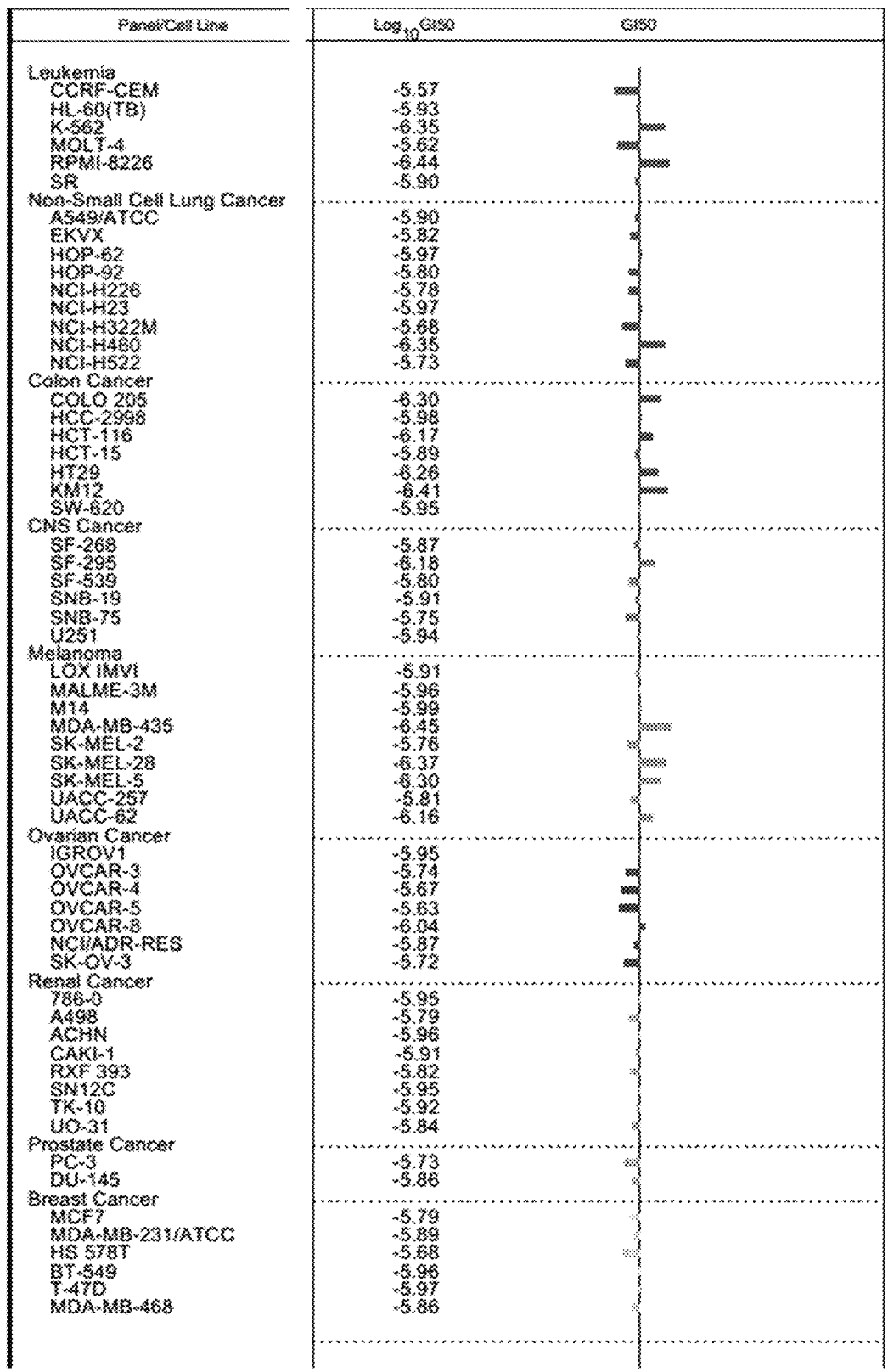
FIG. 3 shows mean graph data for the cancer cell screen described in Example 30.
Figure 3:
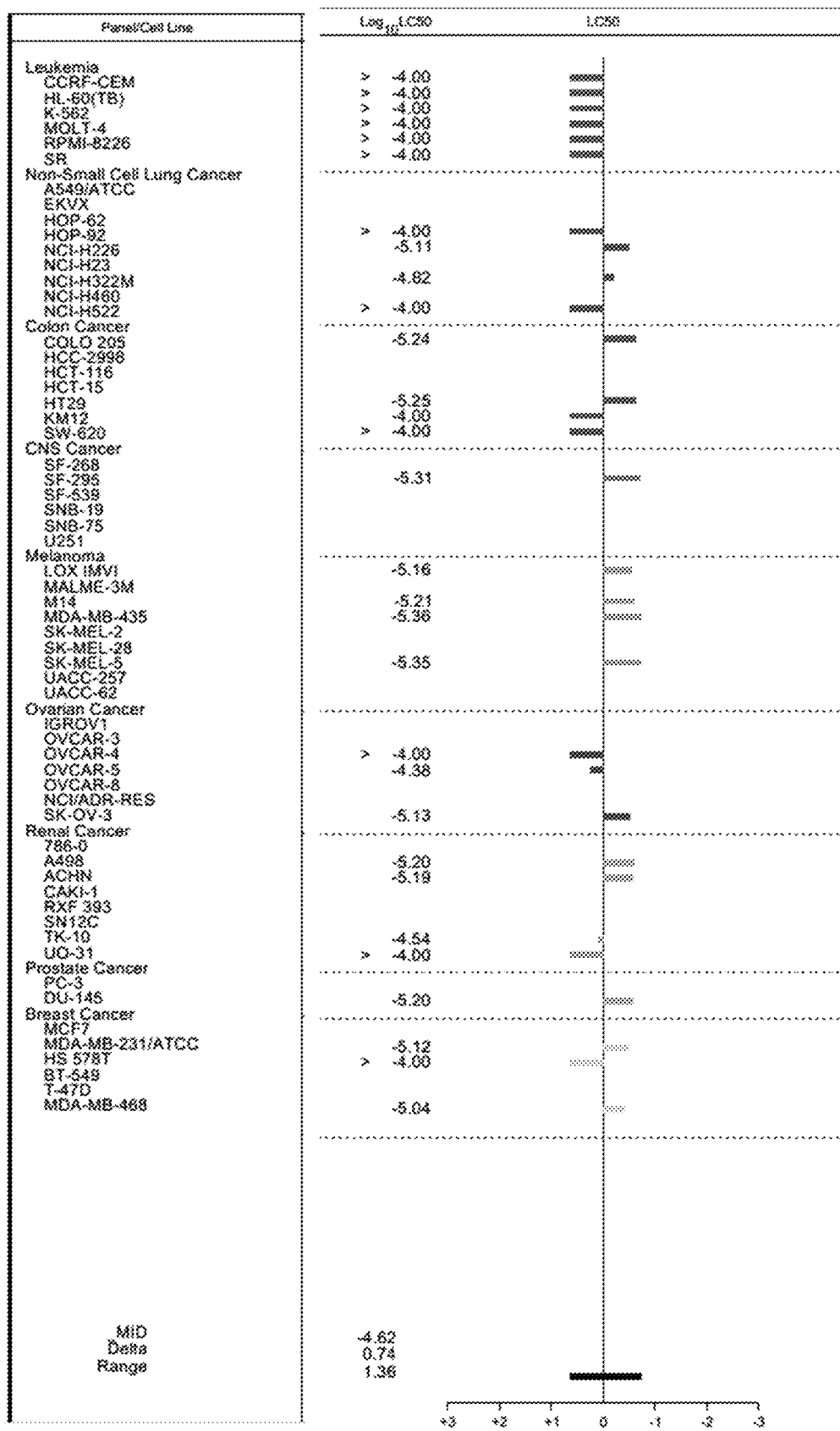
Figure 3:
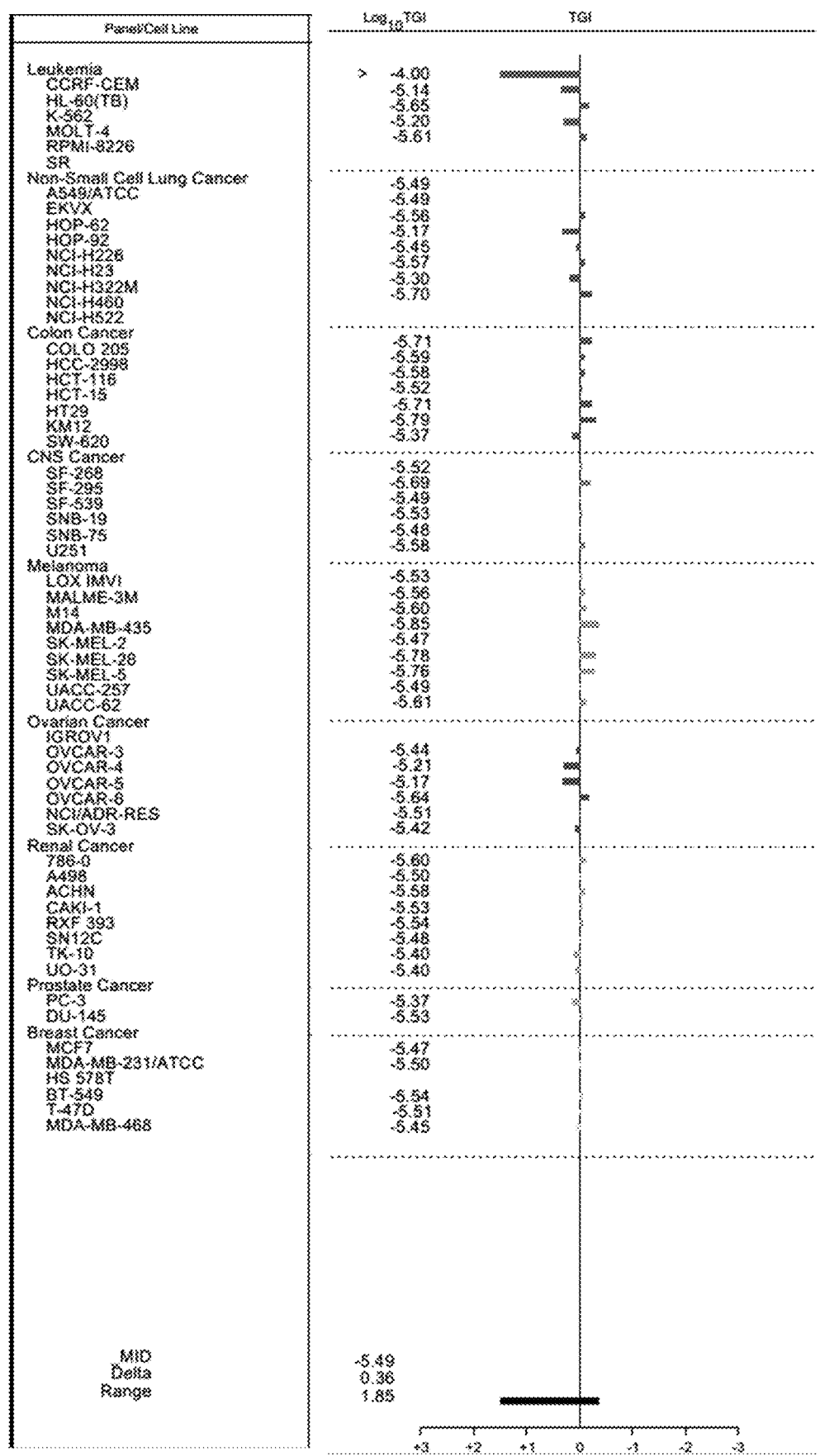

The results of this experiment are shown in Table 22. Dose response curves of cancer cell screen are shown in FIG. 2. The data displaced in mean graph form in shown in FIG. 3.

TABLE 22

Cancer Cell Screen Testing Results.

| | Time | | Mean Optical Densities | Log10 Concentration | | | | Percent Growth | | | | | | |
|---|---|---|---|---|---|---|---|---|---|---|---|---|---|---|
| Panel/Cell Line | Zero | Ctrl | -8.0 | -7.0 | -6.0 | -5.0 | -4.0 | -8.0 | -7.0 | -6.0 | -5.0 | -4.0 | GI50 | TGI | LC50 |
| Leukemia | | | | | | | | | | | | | | | |
| CCRF-CEM | 0.599 | 2.409 | 2.412 | 2.434 | 2.138 | 0.680 | 0.629 | 100 | 101 | 85 | 4 | 2 | 2.72E-6 | >1.00E-4 | >1.00E-4 |
| HL-60(TB) | 0.683 | 1.833 | 1.995 | 1.732 | 1.306 | 0.625 | 0.556 | 114 | 91 | 54 | -8 | -19 | 1.17E-6 | 7.32E-6 | >1.00E-4 |
| K-562 | 0.213 | 1.816 | 1.774 | 1.838 | 0.572 | 0.125 | 0.195 | 97 | 101 | 22 | -42 | -8 | 4.47E-7 | 2.24E-6 | >1.00E-4 |
| MOLT-4 | 0.644 | 1.779 | 1.773 | 1.857 | 1.728 | 0.491 | 0.620 | 99 | 107 | 95 | -24 | -4 | 2.40E-6 | 6.31E-6 | >1.00E-4 |
| RPMI-8226 | 0.706 | 2.261 | 2.304 | 2.095 | 1.004 | 0.499 | 0.661 | 103 | 89 | 19 | -29 | -6 | 3.63E-7 | 2.48E-6 | >1.00E-4 |
| SR | 0.272 | 1.118 | 1.098 | 1.121 | 0.768 | 0.205 | 0.306 | 98 | 100 | 59 | -25 | 4 | 1.27E-6 | — | >1.00E-4 |
| Non-Small Cell Lung Cancer | | | | | | | | | | | | | | | |
| A549/ATCC | 0.412 | 1.816 | 1.804 | 1.755 | 1.281 | 0.165 | 0.224 | 99 | 96 | 62 | -60 | -46 | 1.25E-6 | 3.22E-6 | — |
| EKVX | 0.731 | 1.964 | 1.994 | 1.884 | 1.682 | 0.181 | 0.614 | 102 | 94 | 77 | -75 | -16 | 1.51E-6 | 3.21E-6 | — |
| HOP-62 | 0.504 | 1.597 | 1.569 | 1.533 | 1.093 | 0.152 | 0.334 | 97 | 94 | 54 | -70 | -34 | 1.07E-6 | 2.72E-6 | — |
| HOP-92 | 1.035 | 1.620 | 1.630 | 1.608 | 1.424 | 0.891 | 0.784 | 102 | 98 | 66 | -14 | -24 | 1.60E-6 | 6.71E-6 | >1.00E-4 |
| NCI-H226 | 1.176 | 2.737 | 2.723 | 2.675 | 2.461 | 0.389 | 0.249 | 99 | 96 | 82 | -67 | -79 | 1.65E-6 | 3.56E-6 | 7.70E-6 |
| NCI-H23 | 0.629 | 1.893 | 2.008 | 1.919 | 1.301 | 0.186 | 0.527 | 109 | 102 | 53 | -70 | -16 | 1.06E-6 | 2.69E-6 | — |
| NCI-H322M | 0.687 | 1.686 | 1.730 | 1.673 | 1.612 | 0.410 | 0.042 | 104 | 99 | 93 | -40 | -94 | 2.09E-6 | 4.97E-6 | 1.52E-5 |
| NCI-H460 | 0.226 | 2.446 | 2.507 | 2.273 | 0.822 | 0.086 | 0.207 | 103 | 92 | 27 | -62 | -9 | 4.42E-7 | 2.01E-6 | — |
| NCI-H522 | 0.845 | 2.309 | 2.354 | 2.390 | 2.102 | 0.448 | 0.921 | 103 | 106 | 86 | -47 | 5 | 1.86E-6 | — | >1.00E-4 |
| Colon Cancer | | | | | | | | | | | | | | | |
| COLO 205 | 0.460 | 1.543 | 1.506 | 1.467 | 0.800 | 0.115 | 0.114 | 97 | 93 | 31 | -75 | -75 | 4.98E-7 | 1.97E-6 | 5.82E-6 |
| HCC-2998 | 0.726 | 2.445 | 2.457 | 2.447 | 1.627 | 0.186 | 0.453 | 101 | 100 | 52 | -74 | -38 | 1.04E-6 | 2.59E-6 | — |
| HCT-116 | 0.228 | 1.831 | 1.764 | 1.783 | 0.877 | 0.102 | 0.191 | 96 | 97 | 40 | -55 | -16 | 6.79E-7 | 2.64E-6 | — |
| HCT-15 | 0.289 | 1.908 | 1.943 | 1.850 | 1.349 | 0.080 | 0.173 | 102 | 96 | 65 | -72 | -40 | 1.30E-6 | 2.99E-6 | — |
| HT29 | 0.206 | 1.422 | 1.486 | 1.427 | 0.601 | 0.046 | 0.081 | 105 | 100 | 32 | -78 | -61 | 5.52E-7 | 1.97E-6 | 5.59E-6 |
| KM12 | 0.388 | 1.975 | 2.030 | 1.872 | 0.701 | 0.104 | 0.194 | 103 | 93 | 20 | -73 | -50 | 3.89E-7 | 1.63E-6 | 1.00E-4 |
| SW-620 | 0.256 | 1.962 | 1.994 | 1.835 | 1.176 | 0.175 | 0.191 | 102 | 93 | 54 | -32 | -25 | 1.11E-6 | 4.25E-6 | >1.00E-4 |
| CNS Cancer | | | | | | | | | | | | | | | |
| SF-268 | 0.559 | 1.936 | 1.998 | 1.923 | 1.497 | 0.154 | 0.525 | 104 | 99 | 68 | -73 | -6 | 1.35E-6 | 3.05E-6 | — |
| SF-295 | 0.657 | 2.074 | 2.092 | 1.950 | 1.237 | 0.056 | 0.307 | 101 | 91 | 41 | -91 | -53 | 6.59E-7 | 2.04E-6 | 4.86E-6 |
| SF-539 | 1.010 | 2.830 | 2.890 | 2.752 | 2.520 | 0.191 | 0.562 | 103 | 96 | 83 | -81 | -44 | 1.59E-6 | 3.20E-6 | — |
| SNB-19 | 0.508 | 1.715 | 1.706 | 1.586 | 1.250 | 0.162 | 0.396 | 99 | 89 | 62 | -68 | -22 | 1.23E-6 | 2.98E-6 | — |
| SNB-25 | 0.738 | 1.560 | 1.592 | 1.520 | 1.532 | 0.074 | 0.505 | 104 | 95 | 97 | -90 | -32 | 1.78E-6 | 3.29E-6 | — |
| U251 | 0.329 | 1.543 | 1.533 | 1.526 | 1.046 | 0.059 | 0.285 | 99 | 99 | 59 | -82 | -13 | 1.16E-6 | 2.62E-6 | — |
| Melanoma | | | | | | | | | | | | | | | |
| LOX IMVI | 0.232 | 1.092 | 1.087 | 1.072 | 0.765 | 0.068 | 0.039 | 99 | 98 | 62 | -71 | -83 | 1.23E-6 | 2.93E-6 | 6.98E-6 |
| MALME-3M | 0.656 | 1.129 | 1.182 | 1.159 | 0.915 | 0.195 | 0.525 | 111 | 106 | 55 | -70 | -20 | 1.09E-6 | 2.74E-6 | — |
| M14 | 0.399 | 1.386 | 1.389 | 1.321 | 0.901 | 0.091 | 0.095 | 100 | 93 | 51 | -77 | -76 | 1.02E-6 | 2.49E-6 | 6.12E-6 |

TABLE 22-continued

Cancer Cell Screen Testing Results.

| | Time | | Mean Optical Densities | | | | | Percent Growth | | | | | | | |
|---|---|---|---|---|---|---|---|---|---|---|---|---|---|---|---|
| | | | | | Log10 Concentration | | | | | | | | | | |
| Panel/Cell Line | Zero | Ctrl | −8.0 | −7.0 | −6.0 | −5.0 | −4.0 | −8.0 | −7.0 | −6.0 | −5.0 | −4.0 | GI50 | TGI | LC50 |
| MDA-MB-435 | 0.526 | 2.758 | 2.764 | 2.597 | 0.862 | 0.071 | 0.040 | 100 | 93 | 15 | −87 | −92 | 3.55E−7 | 1.41E−6 | 4.37E−6 |
| SK-MEL-2 | 0.969 | 2.130 | 2.195 | 2.120 | 2.011 | 0.203 | 0.495 | 106 | 99 | 90 | −79 | −49 | 1.72E−6 | 3.40E−6 | — |
| SK-MEL-28 | 0.611 | 1.703 | 1.725 | 1.651 | 0.868 | 0.090 | 0.428 | 102 | 95 | 24 | −85 | −30 | 4.28E−7 | 1.65E−6 | — |
| SK-MEL-5 | 0.826 | 3.135 | 3.135 | 3.055 | 1.515 | 0.058 | 0.166 | 100 | 97 | 30 | −93 | −80 | 4.98E−7 | 1.75E−6 | 4.46E−6 |
| UACC-257 | 1.210 | 2.249 | 2.237 | 2.247 | 2.034 | 0.293 | 0.777 | 99 | 100 | 79 | −76 | −36 | 1.55E−6 | 3.25E−6 | — |
| UACC-62 | 0.835 | 2.769 | 2.762 | 2.712 | 1.634 | 0.292 | 0.810 | 100 | 97 | 41 | −65 | −3 | 6.98E−7 | 2.45E−6 | — |
| Ovarian Cancer | | | | | | | | | | | | | | | |
| IGROV1 | 0.618 | 1.877 | 1.970 | 1.868 | 1.314 | 0.282 | 0.647 | 107 | 99 | 55 | −54 | 2 | 1.12E−6 | — | — |
| OVCAR-3 | 0.278 | 1.015 | 1.044 | 0.971 | 0.956 | 0.079 | 0.200 | 104 | 94 | 92 | −72 | −28 | 1.80E−6 | 3.64E−6 | — |
| OVCAR-4 | 0.645 | 1.504 | 1.511 | 1.388 | 1.388 | 0.498 | 0.592 | 101 | 87 | 86 | −23 | −8 | 2.16E−6 | 6.19E−6 | >1.00E−4 |
| OVCAR-5 | 0.716 | 1.865 | 1.875 | 1.757 | 1.755 | 0.588 | 0.22 | 101 | 91 | 90 | −18 | −69 | 2.36E−6 | 6.80E−6 | 4.18E−5 |
| OVCAR-8 | 0.476 | 1.980 | 1.973 | 1.996 | 1.199 | 0.065 | 0.374 | 100 | 101 | 48 | −86 | −22 | 9.18E−7 | 2.28E−6 | — |
| NCI/ADR-RES | 0.486 | 1.685 | 1.672 | 1.708 | 1.298 | 0.150 | 0.377 | 99 | 102 | 68 | −69 | −22 | 1.35E−6 | 3.12E−6 | — |
| SK-OV-3 | 1.057 | 2.145 | 2.153 | 2.079 | 2.118 | 0.302 | 0.460 | 101 | 94 | 98 | −71 | −56 | 1.91E−6 | 3.78E−6 | 7.47E−6 |
| Renal Cancer | | | | | | | | | | | | | | | |
| 786-0 | 0.446 | 1.789 | 1.832 | 1.684 | 1.217 | 0.060 | 0.251 | 103 | 92 | 57 | −87 | −44 | 1.13E−6 | 2.50E−6 | — |
| A498 | 1.471 | 2.313 | 2.301 | 2.270 | 2.196 | 0.221 | 0.219 | 99 | 95 | 86 | −85 | −85 | 1.63E−6 | 3.19E−6 | 6.24E−6 |
| ACHN | 0.394 | 1.754 | 1.777 | 1.661 | 1.150 | 0.098 | 0.170 | 102 | 93 | 56 | −75 | −57 | 1.10E−6 | 2.66E−6 | 6.41E−6 |
| CAKI-1 | 0.669 | 2.227 | 2.235 | 2.075 | 1.637 | 0.204 | 0.388 | 100 | 90 | 62 | −70 | −42 | 1.24E−6 | 2.96E−6 | — |
| RXF 393 | 0.621 | 1.266 | 1.246 | 1.252 | 1.143 | 0.038 | 0.509 | 97 | 98 | 81 | −94 | −18 | 1.50E−6 | 2.90E−6 | — |
| SN12C | 0.367 | 1.435 | 1.436 | 1.376 | 0.955 | 0.179 | 0.295 | 100 | 94 | 55 | −51 | −20 | 1.12E−6 | 3.29E−6 | — |
| TK-10 | 0.855 | 2.088 | 2.154 | 2.111 | 1.567 | 0.527 | 0.313 | 105 | 102 | 58 | −38 | −63 | 1.20E−6 | 3.99E−6 | 2.92E−5 |
| UO-31 | 0.627 | 1.739 | 1.719 | 1.738 | 1.392 | 0.338 | 0.532 | 98 | 100 | 69 | −46 | −15 | 1.46E−6 | 3.97E−6 | >1.00E−4 |
| Prostate Cancer | | | | | | | | | | | | | | | |
| PC-3 | 0.470 | 1.297 | 1.314 | 1.235 | 1.201 | 0.225 | 0.262 | 102 | 92 | 88 | −52 | −44 | 1.88E−6 | 4.26E−6 | — |
| DU-145 | 0.383 | 1.597 | 1.665 | 1.590 | 1.257 | 0.077 | 0.040 | 106 | 99 | 72 | −80 | −90 | 1.40E−6 | 2.98E−6 | 6.36E−6 |
| Breast Cancer | | | | | | | | | | | | | | | |
| MCF7 | 0.435 | 2.145 | 2.248 | 2.095 | 1.864 | 0.117 | 0.253 | 106 | 97 | 84 | −73 | −42 | 1.64E−6 | 3.41E−6 | — |
| MDA-MB-231/ATCC | 0.452 | 1.176 | 1.173 | 1.124 | 0.922 | 0.157 | 0.197 | 100 | 93 | 65 | −65 | −57 | 1.30E−6 | 3.15E−6 | 7.63E−6 |
| HS 578T | 0.805 | 1.702 | 1.724 | 1.670 | 1.566 | 0.620 | 1.032 | 102 | 96 | 85 | −23 | 25 | 2.10E−6 | — | >1.00E−4 |
| BT-549 | 0.895 | 1.675 | 1.739 | 1.558 | 1.325 | 0.323 | 0.740 | 108 | 85 | 55 | −64 | −17 | 1.10E−6 | 2.90E−6 | — |
| T-47D | 0.754 | 1.519 | 1.537 | 1.481 | 1.163 | 0.334 | 0.488 | 102 | 95 | 53 | −56 | −35 | 1.08E−6 | 3.09E−6 | — |
| MDA-MB-468 | 0.788 | 1.420 | 1.437 | 1.367 | 1.212 | 0.360 | 0.377 | 103 | 92 | 67 | −54 | −52 | 1.38E−6 | 3.57E−6 | 9.20E−6 |

*Density units are in μg/ml.

Various modifications of the invention, in addition to those described herein, will be apparent to those skilled in the art from the foregoing description. Such modifications are also intended to fall within the scope of the appended claims. Each reference cited in the present application, including all patents, patent applications, and non-patent literature, is incorporated by reference in its entirety.

What is claimed is:

1. A Formula I polymer fraction having an average molecular weight of from about 780 Da to about 5700 Da and a molecular distribution of less than about 10 kDa, Formula I is:

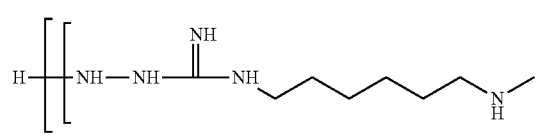

wherein n is 1-3; m is 4-14; z is 1-6; and X is an acid.

2. The polymer fraction of claim 1 which is substantially free of other polymer components.

3. The polymer fraction of claim 1, wherein X is selected from HCl, H$_2$SO$_4$, or AcOH.

4. The polymer fraction of claim 1, wherein the median molecular weight range of the polymer fraction is from about 1330 Da to about 3500 Da.

5. The polymer fraction of claim 1, selected from:

| Example No. | Polymer Fraction |
|---|---|
| 1 | 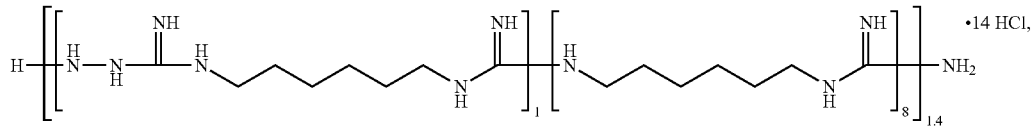<br>the average molecular weight is 1850 (±10%) Da and the molecular distribution less than about 3000 Da; |
| 2 | 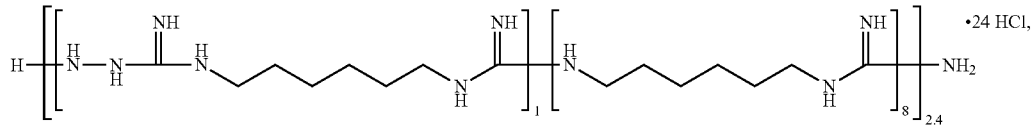<br>the average molecular weight is 3170 (±10%) Da and the molecular distribution is less than about 10 000 Da; |
| 3 | 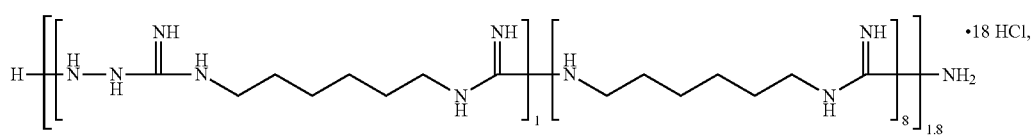<br>the average molecular weight is 2300 (±10%) Da and the molecular distribution is between about 1000 and about 3000 Da; |
| 4 | 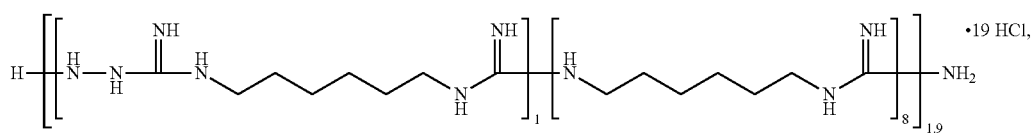<br>the average molecular weight is 2500 (+10%) Da and the molecular distribution is between about 2000 and about 3000 Da; |
| 5 | 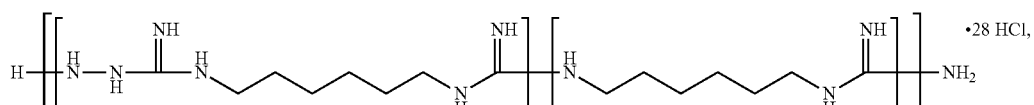<br>the average molecular weight is 3680 (+10%) Da and the molecular distribution is between about 3000 and about 5000 Da; |
| 6 | 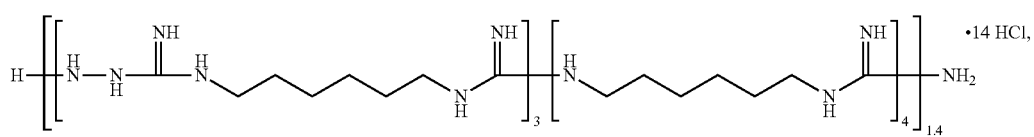<br>the average molecular weight is 1600 (+10%) Da the molecular weight distribution is less than about 3000 Da; |
| 7 | 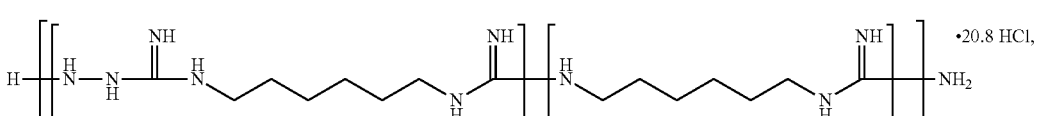<br>the average molecular weight is 2800 (+10%) Da and the molecular distribution is less than about 10 000 Da |
| 8 | 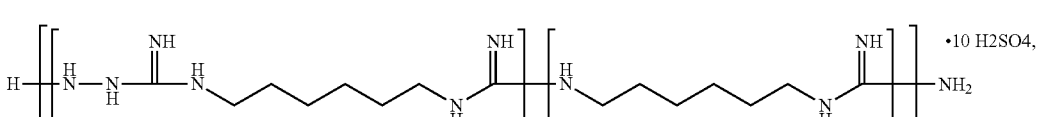<br>the average molecular weight is 2600 (+10%) Da and the molecular distribution is less than 10 000 Da; |

-continued

| Example No. | Polymer Fraction |
|---|---|
| 9 | 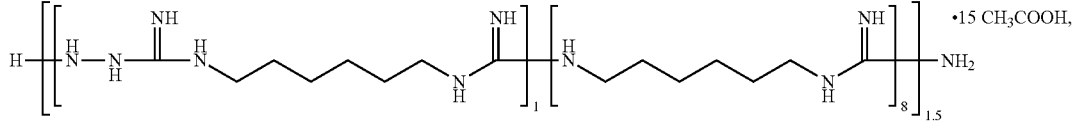<br>the average molecular weight is 2000 (+10%) Da and the molecular distribution is less than about 3 000 Da; |
| 10 | 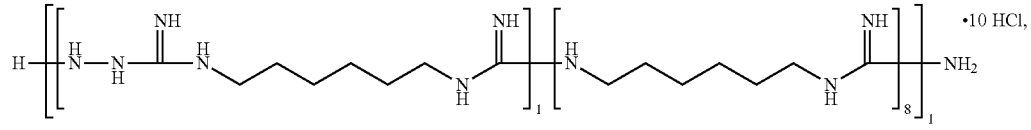<br>the average molecular weight is 1330 (+10%) Da and the molecular distribution is less than about 2 000 Da; |
| 11 | 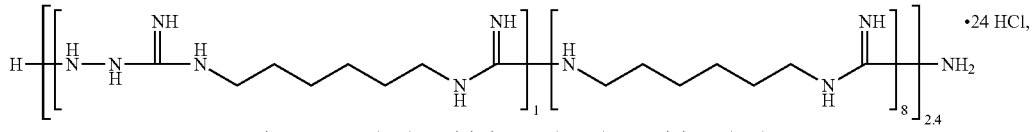<br>the average molecular weight is 3100 (+10%) Da and the molecular distribution is less than about 5 000 Da; |
| 12 | 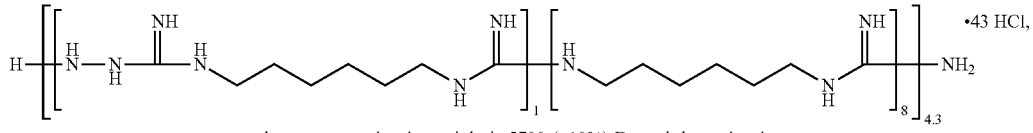<br>the average molecular weight is 5700 (+10%) Da and the molecular distribution is between about 5000 to about 10 000 Da; and |
| 13 | 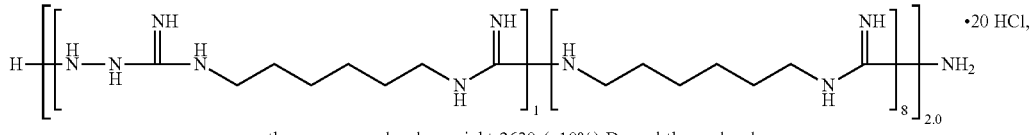<br>the average molecular weight 2630 (+10%) Da and the molecular distribution between about 2000 to about 10 000 Da. |

6. A pharmaceutical composition comprising the polymer fraction of claim 1 and a pharmaceutical excipient.

7. A method of preparing the polymer fraction of claim 1 comprising:
reacting hexamethylenediamine with a guanidine salt and a compound selected from the group consisting of: hydrazine hydrate, semicarbazide, semicarbazide chlorhydrate, carbohydrazide, and aminoguanidine hydrochloride, at a temperature of 175° C. to 195° C.; and isolating the polymer fraction by dialysis.

8. A Formula I polymer fraction having an average molecular weight of from about 780 Da to about 5700 Da and a molecular distribution of less than about 10 kDa, Formula I is:

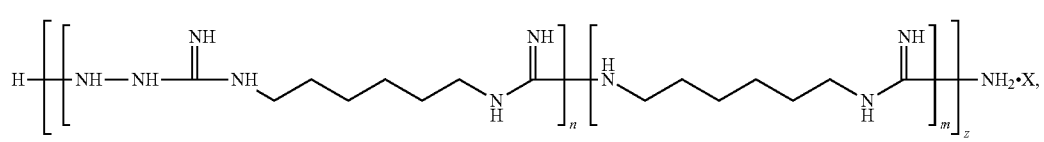

wherein n is 1-3; m is 4-14; z is 1-6; and X is an acid, the polymer fraction being prepared by a process comprising reacting hexamethylenediamine with a guanidine salt and a compound selected from the group consisting of: hydrazine hydrate, semicarbazide, semicarbazide chlorhydrate, carbohydrazide, and aminoguanidine hydrochloride, at a temperature of 175° C. to 195° C.; and isolating the polymer fraction by dialysis.

9. A method of treating an infection in a subject in need thereof, comprising administering to the subject an effective amount of the polymer fraction of claim 1.

10. The method of claim 9, wherein the infection is caused by an agent selected from the group consisting of bacterial, fungal, viral, and protozoal agents.

11. The method of claim 9, wherein the infection is selected from the group consisting of: a mixed infection, a systemic infection, a dental infection, a skin and soft tissue infection or an infection of a wound/ulcers, a mucosal infection, a respiratory tract infection, a lung infection, an infection of abscesses, a sinusitis, and an ophthalmologic infection.

12. The method of claim 11, wherein the lung infection is caused by mixed bacterial, fungal and/or viral strains.

13. The method of claim 9, wherein the lung infection is associated with Chronic Obstructive Pulmonary Disease (COPD), pneumonia, cystic fibrosis infection, and Ventilator-associated pneumonia (VAP).

14. The method of claim 9, wherein the polymer fraction is administered locally, instilled, administered topically, administered enterally or administered parenterally.

15. The method of claim 9, wherein the polymer fraction is administered in combination with other antimicrobial drugs.

* * * * *